(12) United States Patent
Karger et al.

US007427479B2

(10) Patent No.: US 7,427,479 B2
(45) Date of Patent: Sep. 23, 2008

(54) METHODS AND KITS FOR IDENTIFYING TARGET NUCLEOTIDES IN MIXED POPULATIONS

(75) Inventors: Achim E. Karger, Foster City, CA (US); Elena V. Bolchakova, Union City, CA (US)

(73) Assignee: Applera Corporation, Foster City, CA (US)

( * ) Notice: Subject to any disclaimer, the term of this patent is extended or adjusted under 35 U.S.C. 154(b) by 253 days.

(21) Appl. No.: 11/118,973

(22) Filed: Apr. 29, 2005

(65) Prior Publication Data

US 2006/0003351 A1 Jan. 5, 2006

Related U.S. Application Data

(60) Provisional application No. 60/567,068, filed on Apr. 30, 2004.

(51) Int. Cl.
*C12Q 1/68* (2006.01)
*C12P 19/34* (2006.01)
(52) U.S. Cl. .......................................... 435/6; 435/91.2
(58) Field of Classification Search ........................ None
See application file for complete search history.

(56) References Cited

U.S. PATENT DOCUMENTS

| 4,988,617 | A | | 1/1991 | Landegren et al. |
| 5,700,672 | A | | 12/1997 | Mathur et al. |
| 6,130,073 | A | * | 10/2000 | Eggerding ................ 435/91.2 |
| 6,331,393 | B1 | | 12/2001 | Laird et al. |

FOREIGN PATENT DOCUMENTS

| WO | WO 91/17239 A1 | 11/1991 |
| WO | WO 96/15271 A1 | 5/1996 |
| WO | WO 98/03673 | 1/1998 |

OTHER PUBLICATIONS

M. Khanna et al., "Multiplex PCR/LDR for Detection of K-ras Mutations in Primary Colon Tumors", Oncogene (1999), vol. 18, pp. 27-38, XP009006346.
Partial International Search Report issued in International Application No. PCT/US2005/015027 on Dec. 12, 2006, 10 pages.
M. Angers et al., "Optimal Conditions To Use Pfu exo DNA Polymerase For Highly Efficient Ligation-Mediated Polymerase Chain Reaction Protocols", Nucleic Acids Research, 2001, vol. 29, No. 16 e83, pp. 1-11.
L. Aravind et al., "Prokaryotic Homologs Of The Eukatyotic DNA-End-Binding Protein Ku, Novel Domains In The Ku Protein And Prediction Of A Prokaryotic Double-Strand Break Repair System", Genome Research, 2001, vol. 11, pp. 1365-1374.
F. Barany, "Genetic Disease Detection And DNA Amplifcation Using Cloned Thermostable Ligase", Proc. Natl. Acad. Sci. USA, vol. 88, Jan. 1991, pp. 189-193.

W. Bi et al., "CCR: A Rapid And Simple Approach For Mutation Detection", Nucleic Acids Research, 1997, vol. 25, No. 14, pp. 2949-2951.
W. Cao, "Recent Developments In Ligase-Mediated Amplification And Detection", Trends in Biotechnology, vol. 22, No. 1, Jan. 2004, pp. 38-44.
C. Eads et al., "MethyLight: A High-Throughput Assay To Measure DNA Methylation", Nucleic Acids Research, 2000, vol. 28, No. 8 e32, pp. i-viii.
D. Faulhammer et al., "Fidelity Of Enzymatic Ligation For DNA Computing", Journal of Computational Biology, vol. 7 No. 6, 2000, pp. 839-848.
M. Fraga et al., "DNA Methylation: A Profile Of Methods And Applications" BioTechniques, vol. 33, Sep. 2002, pp. 632-649.
C. Goffin et al., "Nicks 3' 5' To AP Sites Or To Mispaired Bases, And One-Nucleotide Gaps Can Be Sealed By T4 DNA Ligase", Nucleic Acids Research, 1987, vol. 15, No. 21, pp. 8755-8771
J. Herman et al., "Methylation-Specific PCR: A Novel PCR Assay For Methylation Status Of CpG Islands", Proc. Natl. Acad. Sci. USA, vol. 93, Sep. 1996, pp. 9821-9826.
J. N. Housby et al., "Optimised Ligation Of Oligonucleotides By Thermal Ligases: Comparison Of Thermus Scotoductus And Rhodothermus Marinus DNA Ligases To Other Thermophilic Ligases", Nucleic Acids Research, 2000, vol. 28, No. 3 e10, pp. i-v.
J. N. Housby et al., "Fidelity Of DNA Ligation: A Novel Experimental Approach Based On the Polymerisation Of Libraries Of Oligonucleotides", Nucleic Acids Research, 1998, vol. 26, No. 18, pp. 4259-4266.
I. Husain et al., "Purification And Characterization Of DNA Ligase III From Bovine Testes", The Journal of Biological Chemistry, vol. 270, No. 16, Apr. 21, 1995, pp. 9683-9690.
S. Jeon et al., "A Novel ADP-Dependent DNA Ligase From *Aeropyrum Pernix* K1", FEBS Letters 550, Jul. 2003, pp. 69-73.
H. Klenk et al., "The Complete Genome Sequence Of The Hyperthermophilic, Sulphate-Reducing Archaeon Archeaoglobus Fulgidus", Nature, vol. 390, Nov. 1997, pp. 364-375.
H. Klenk et al., "The Complete Genome Sequence Of the Hyperthermiphilic Sulphate-Reducing Archaeon Archaeoglobus Fulgidus", Nature, vol. 394, Jul. 2, 1998, pp. 101.
P. Laird, "The Power And The Promise Of DNA Methylation Markers", Nature Reviews, Cancer, vol. 3, Apr. 2003, pp. 253-266.
U. Landegren et al., "A Ligase-Mediated Gene Detection Technique", Science, New Series, vol. 241, No. 4869, Aug. 26, 1988, pp. 1077-1080.
J. Lou et al., "Improving The Fidelity Of Thermus Thermophilus DNA Ligase", Nucleic Acids Research, 1996, vol. 24, No. 14, pp. 3071-3078.
I. Martin et al., "ATP-Dependent DNA Ligases", Genome Biology 2002, vol. 3(4) :Reviews, pp. 3005.1-3005.7.

(Continued)

*Primary Examiner*—James Martinell
(74) *Attorney, Agent, or Firm*—Lin Sun-Hoffman

(57) ABSTRACT

Ligation-based methods and kits are disclosed for identifying at least two target nucleotides in a mixed population sample, that is a sample that contains or potentially contains target nucleic acid sequences from more than one source. Typically, two ligation reaction compositions are formed, ligation products generated, and the ligation products or their surrogates are analyzed to identify target nucleotides in the mixed population sample. In certain embodiments, the target nucleic acid sequences, the ligation products, or both are amplified. In certain embodiments, multiplex amplification and/or ligation reactions are performed.

43 Claims, 2 Drawing Sheets

OTHER PUBLICATIONS

M. Nakatani et al., "Substrate Recognition And Fidelity Of Strand Joining By An Archaeal DNA Ligase", Eur. J. Biochem. vol. 269, 2002, pp. 650-656, FEBS 2002.

O. Okochi et al., "Detection Of Mitochondrial DNA Alterations In The Serum Of Hepatocellular Carcinoma Patients", Clinical Cancer Research, vol. 8, Sep. 2002, pp. 2875-2878.

C, Pritchard et al., "Effects Of Base Mismatches On Joining Of Short Oligodeoxynucleotides By DNA Ligases", Nucleic Acids Research, 1997, vol. 25, No. 17, pp. 3403-3407.

T. Rein et al., "Identifying 5-Methylcytosine And Related Modifications In DNA Genomes", Nucleic Acids Research, 1998, vol. 26, No. 10, pp. 2255-2264.

S. Shuman, "Vaccinia Virus DNA Ligase: Specificity, Fidelity, And Inhibition"., Biochemistry 1995, vol. 34, pp. 16138-16147.

V. Sriskanda et al., "Characterization Of An ATP-Dependent DNA Ligase From The Thermophilic Archaeon Methanobacterium Thermoautotrophicum", Nucleic Acids Research, 2000, vol. 28, No. 11, pp. 2221-2228.

V. Sriskanda et al., "Chlorella Virus DNA Ligase: Nick Recognition And Mutational Analysis", Nucleic Acids Research, 1998, vol. 26, No. 2, pp. 525-531.

V. Sriskanda et al., "Specificity And Fidelity Of Strand Joining By Chlorella Virus DNA Ligase", Nucleic Acids Research, 1998, vol. 26, No. 15, pp. 3536-3541.

V. Sriskanda et al., "NAD+-Dependent DNA Ligase Encoded By A Eukaryotic Virus", The Journal of Biological Chemistry, vol. 276, No. 39, Sep. 28, 2001, pp. 36100-36109.

J. Tong et al., "Biochemical Properties Of A High Fidelity DNA Ligase From Thermus Species AK16D", Nucleic Acids Research, 1999, vol. 27, No. 3, pp. 788-794.

J. Tong et al., "Ligation Reaction Specificities Of An $NAD^+$-Dependent DNA Ligase From The Hyperthermophile Aquifex Aeolicus", Nucleic Acids Research 2000, vol. 28, No. 6, pp. 1447-1454.

G. Weller et al., "A Family Of DNA Repair Ligases In Bacteria", FEBS: Letters 505, 2001, pp. 340-342.

M. Zirvi et al, "Improved Fidelity Of Thermostable Ligases For Detection Of Microsatellite Repeat Sequences Using Nucleoside Analogs", Nucleic Acids Research, 1999, vol. 27, No. 24 e41, pp. i-vii.

M. Zirvi et al., "Ligase-Based Detection Of Mononucleotide Repeat Sequences", Nucleic Acids Research, 1999, vol. 27, No. 24 e40, pp. i-viii.

U.S. Appl. No. 11/119,069, filed Apr. 29, 2005.

U.S. Appl. No. 11/119,985, filed May 2, 2005.

* cited by examiner

METHODS AND KITS FOR IDENTIFYING TARGET NUCLEOTIDES IN MIXED POPULATIONS

CROSS-REFERENCE TO RELATED APPLICATIONS

This application claims a priority benefit under 35 U.S.C. § 119(e) from U.S. patent application Ser. No. 60/567,068, filed Apr. 30, 2004, which is incorporated herein by reference

FIELD

The present teachings generally relate to compositions, methods, and kits for detecting target nucleic acid sequences in a mixed or potentially mixed nucleic acid sample. Compositions, methods and kits for identifying target nucleotides using at least two ligation reaction compositions are also disclosed. In certain embodiments, at least two ligases are used decrease the generation of certain misligation products.

BACKGROUND

The occurrence or potential occurrence of samples comprising mixed nucleic acid sequences, i.e., DNA and/or RNA from more than one donor, present an ever-increasing problem in characterizing such sample. The terrorist events of Sep. 11, 2001 resulted in the need to positively identify thousands of human remains, including over 2500 at the World Trade Center alone. Similar forensics identification problems may also occur at other mass fatality incidents, whether the result of terrorist acts, accidents such as commercial plane crashes, or natural disasters, such as earthquakes. It is possible that a "sample" obtained from a mass fatality incident may contain nucleic acid from more than one individual, which could lead to misidentification.

Mixed nucleic acid samples can also present identification problems in a variety of other circumstances, including without limitation: clinical samples, for example cultures comprising normal flora as well as pathogenic microorganisms, typically related to one or more members of the normal flora; biopsy samples obtained from cancerous tissues that may comprise a mixture of normal and malignant cells and/or at least one subset of drug sensitive cells and at least one subset of drug resistant cells; samples from patients undergoing drug therapy that comprise mixtures of "wild-type" microorganisms (or viruses) and emerging drug-resistant strains, including without limitation, the human immunodeficiency virus (HIV), hepatitis C virus (HCV), *Mycobacterium tuberculosis*, and venereal diseases, such as *Neisseria gonnorrhoeae, Chlamydia trachomatis, Treponema pallidum*, and the like; and samples from crime scenes, such as fingerprints, blood, semen, and the like. A variety of analytical techniques have been developed to detect and characterize nucleic acid sequences present in a sample, including without limitation, ligation-based and/or amplification-based assays.

Ligase catalyzed reactions form the basis for several current assay techniques, for example but not limited to, the oligonucleotide ligation assay (OLA), the ligase chain reaction (LCR), the ligase detection reaction (LDR) and combination assays such as the OLA coupled with the polymerase chain reaction (PCR), e.g., OLA-PCR and PCR-OLA, the Combined Chain Reaction (CCR; a combination of PCR and LCR) and PCR-LDR (see, e.g., Landegren et al., Science 241:1077-80, 1988; Barany, Proc. Natl. Acad. Sci. 88:189-93, 1991; Grossman et al., Nucl. Acids Res. 22(21):4527-34, 1994; Bi and Stambrook, Nucl. Acids Res. 25(14):2949-51, 1997; Zirvi et al., Nucl. Acids Res., 27(24):e40, 1999; U.S. Pat. No. 4,988,617; and PCT Publication Nos. WO 97/31256 and WO 01/92579). Such assays have been used for single nucleotide polymorphism (SNP) analysis, SNP genotyping, mutation detection, identification of single copy genes, detecting microsatellite repeat sequences, and DNA adduct mapping, among other things.

The accuracy of these ligation-based assays generally depend on (1) the fidelity of the ligase to distinguish (a) potential ligation sites where both the upstream and downstream probes are correctly base-paired or matched with the template to which they are hybridized from (b) potential ligation sites where at least one nucleotide of at least one probe is not correctly base-paired with the template, sometimes referred to as mismatched, (2) reaction conditions that preclude or minimize hybridization of mismatched probes, or (3) both (see, e.g., Landegren et al., Science 241:1077-80, 1988; Barany, Proc. Natl. Acad. Sci. 88:189-93, 1991). Generally, a high fidelity ligase, i.e., one that catalyzes the ligation of correctly base-paired sequences but does not ligate mismatched sequences is desired (see, e.g., Barany, Proc. Natl. Acad. Sci. 88:189-93, 1991; Luo et al., Nucl. Acids Res. 24(14):3071-78, 1996; and Housby et al., Nucl. Acids Res. 28(3):e10, 2000). Additionally, since these ligation-based assays typically include thermocycling, thermostable ligases are generally preferred (see, e.g., Cao, Trends in Biotechnol 22(1): 38-44, 2004).

While these ligation-based assays rely in part on the fidelity of the enzyme to distinguish properly base-paired from mismatched probes, ligase fidelity is reportedly highly variable, depending on the properties of the particular enzyme, the identity of the mismatched nucleotides, the location of the mismatched nucleotides relative to the ligation junction (also known as the ligation site), the sequence context around the ligation junction, cofactors, and reaction conditions, among other things. The fidelity of several known ligases, based on for example the evaluation of mismatch ligation or ligation rates, has been reported. For example, the $NAD^+$-dependent ligase from the hyperthermophilic bacteria *Aquifex aeolicus* (Aae) reportedly generates detectable 3' misligation products with C:A, T:G, and G:T mismatches (Tong et al., Nucl. Acids Res. 28(6):1447-54, 2000); a partially purified preparation of bovine DNA ligase III reportedly generated detectable 3' misligation products with C:T, G:T, and T:G mismatches, while human ligase I generated detectable 3'misligation products with C:T and G:T mismatches, but not T:G mismatches (Husain et al., J. Biol. Chem. 270(16):9683-90, 1995); and the DNA ligase from the thermophilic bacteria *Thermus thermophilus* (Tth) reportedly generates detectable levels of 3' misligation products with T:G and G:T mismatches (Luo et al., Nucl. Acids Res. 24(14):3071-78, 1996). Bacteriophage T4 DNA ligase reportedly generates detectable misligation products with a wide range of mismatched substrates and appears to have lower fidelity than *Thermus* species ligases by at least one to two orders of magnitude (Landegren et al., Science 241:1077-80, 1988; Tong et al., Nucl. Acids Res. 27(3):788-94, 1999).

Ligase fidelity studies to date generally demonstrate a high degree of substrate specificity with certain mismatches, while misligation products are generated with other mismatched substrate-ligation probe complexes. Thus, ligases tend to have characteristic misligation patterns that can, at least in certain instances, be distinguishing (see, e.g., Sriskanda and Shuman, Nucl. Acids Res. 26(15):3536-41; and Tong et al., Nucl. Acids Res. 28(6):1447-54, 2000). Thus, in certain instances it may be desirable to have a ligase that either will or will not generate detectable misligation products, based on the intended application.

The reliability of certain ligation-based assays, particularly those that employ two or more alternate allele- or target-specific oligonucleotides for discriminating between or more two target nucleotides, may be affected by the tendency of the ligase to generate background misligation products. For example without limitation, an illustrative OLA for analyzing a biallelic SNP site may employ a single species of downstream oligonucleotide (sometimes referred to as a locus-specific oligo or LSO) and two alternate species of upstream oligonucleotides (sometimes referred to as allele-specific oligos or ASOs) that differ in their template-specific portions by, for example, the 3' terminal nucleotide, with each of the upstream oligonucleotide species corresponding to one of the two alternate SNP site alleles being interrogated. Depending on, among other things, the ligase employed; the identity of the mismatched nucleotide(s) and the "corresponding" template nucleotide(s); the sequence context around the ligation junction; the concentration of template, ligation probes, and/or ligase; and the ligation reaction conditions, a misligation product may be formed (or the generation of misligation products may also be avoided or at least minimized). Depending, at least in part, on the amount of misligation product formed, the sample being interrogated, and the sensitivity of the detection technique employed, the misligation product may result in an inaccurate characterization of the sample, including without limitation misdiagnosis and/or misidentification.

SUMMARY

The current teachings provide methods and kits for identifying two or more target nucleotides, including without limitation, a first target nucleotide and a second target nucleotide, in one or more samples that contain or potentially contain nucleic acid sequences from more than one organism, more than one virus, or more than one type of cell, or combinations thereof. According to the current teachings, the presence of, the absence of, or quantity of at least two target nucleotides is determined and the corresponding organism, virus, or cell type can be identified or at least tentatively identified. The current teachings are also directed to identifying the presence or absence of at least two different target nucleotides in a sample that is obtained from a single individual, including without limitation, distinguishing between different alleles at one or more SNP sites, identifying the presence or absence of at least one point mutation, at least one chromosomal translocation, determining the amount of transformed cells in a cancerous tissue, the amount of drug-resistant cells in a patient undergoing chemotherapy, and the like.

When used to determine the genotype of a single individual at a particular bi-allelic SNP, the presence of low levels of detectable misligation product may be tolerable, provided that the levels misligation product are not high enough to interfere with identifying whether the individual is hetero- or homozygous at the SNP site being evaluated (see, e.g., J. Fitness, The NEB Transcript 11:10-11, 2001). For example, for an illustrative G/T SNP site, results of 90% G in the presence of 10% T misligation product would likely be evaluated as the individual is homozygous G at that allele. The generation of misligation products can not be so easily dismissed if, for example, the sample being analyzed contains or potentially contains target nucleic acid sequences from more than one individual, organism, virus, type of cell, or the like. For illustration purposes, a particular marker in a sample obtained from a patient with gastrointestinal problems is evaluated in a ligation-based assay to determine whether the sample contains "wild-type" *E. coli*, part of the normal intestinal flora, or enterotoxigenic *E. coli* (ETEC). Assuming that the same 90:10 results were obtained, does that mean that the sample contains 90% *E. coli* and 10% ETEC (i.e., a mixed population) or is the 10% result due to the presence of a misligation product?

The present teachings are directed to methods and kits for identifying target nucleotides based on ligating oligonucleotide probes, where the probes can but need not comprise nucleotide analogs, including modified nucleotides, and detecting and/or quantifying the ligation products or their surrogates to identify the corresponding target nucleotides. In certain embodiments, detectable misligation products are generated; in certain embodiments, detectable misligation products are at least decreased and preferably are not generated. One can enhance the generation of misligation product using a ligase under reaction conditions and with reagents where that particular ligase is prone to misligation. Alternatively, one can decrease or avoid generating misligation products using a particular ligase under reaction conditions and using reagents where that ligase is at least less prone to generating misligation products. The particular ligase are but not limited to Taq ligase, *Thermus* species ligase AK16D, Tth ligase, Tsc ligase, Tfi ligase, or combinations thereof.

While characterizing the ligase derived from the hyperthermostable archaea *Archaeoglobus fulgidus* (Afu), the applicants made the unexpected finding that the misligation pattern of isolated recombinant Afu ligase is markedly different from other known ligases. For example, using M13-derived oligonucleotide probes and synthetic target nucleic acid sequences, the ligases from *Thermus aquaticus* (Taq) and *Thermus* species AK16D ("AK16D") were much more prone to 3'G:T misligation compared to Afu ligase, while Afu ligase was more prone to misligations comprising a C nucleotide than either of these *Thermus* ligases under the same conditions (see, e.g., Table 1). Applicants are unaware of any published reports of a thermostable ligase that can effectively discriminates against 3'T:G mismatched substrates, but can produce detectable misligation products with 3'T:C substrates (see also co-filed U.S. Provisional Patent Application Ser. No. 60/567,120, filed Apr. 30, 2004, for "Compositions, Methods, and Kits for (Mis)ligating Oligonucleotides, by Karger et al., and U.S. Provisional Patent Application Ser. No. 60/567,396, filed April 30, 2005, for "Methods and Kits for Methylation Detection," by Andersen et al.

In certain embodiments, methods for generating ligation products are disclosed, wherein a first ligation reaction composition comprising at least one probe set (or at least one first probe and at least one corresponding second probe), at least one target nucleic acid sequence, and Afu ligase, including but not limited to at least one enzymatically active mutant or variant thereof, is formed and incubated under appropriate conditions to generate at least one first ligation product. In certain embodiments, a second ligation reaction composition comprising at least one probe set (or at least one first probe and at least one corresponding second probe), at least one target nucleic acid sequence, and at least one second ligase, including but not limited to at least one enzymatically active mutant or variant thereof, is formed and incubated under appropriate conditions to generate at least one second ligation product, wherein the at least one second ligase is typically not Afu ligase. Methods for amplifying such ligation products are disclosed. Methods for generating at least one digested ligation product, at least one amplified digested ligation product, or combinations thereof, are also disclosed. In certain embodiments, amplifying is performed before the ligating, before the digesting, or before the ligating and before the digesting. In certain embodiments, the amplifying is performed after the ligating, after the digesting, or after the ligating and after the digesting. In certain embodiments, at least one ligation product, at least one ligation product surrogate (e.g., at least one amplified ligation product, at least one digested ligation product, at least one amplified digested ligation product, where an "amplified digested ligation product" includes both a ligation product that is first amplified, then digested; and a ligation product that is first digested, then amplified), or combinations thereof are detected and evaluated to identify the presence of and/or the quantity of a specific target nucleotide in the mixed population sample.

In certain embodiments, genomic DNA (gDNA) serves as the ligation template. In certain embodiments, gDNA is amplified and the amplified DNA serves as the ligation template, either in addition to or in place of the gDNA. Within the scope of the teachings are large-scale multiplex analyses of target nucleic acid sequences, including multiplex ligation steps, multiplex amplification steps, or both multiplex ligation steps and multiplex amplification steps.

In certain embodiments, methods for generating at least one ligation product are provided, wherein at least one target nucleic acid sequence is combined with at least one probe set for each target sequence to be interrogated, and at least one ligase to form a ligation reaction composition. The at least one probe set comprises at least one first probe comprising at least one first target-specific portion, and at least one second probe comprising at least one second target-specific portion. The probes in each set are suitable for ligation together when hybridized adjacent to one another on a complementary target sequence, e.g., the end of the upstream probe nearest the ligation site includes a 3' OH group and the end of the downstream probe nearest the ligation site includes a 5' phosphate group. This ligation reaction composition is subjected to at least one cycle of ligation, wherein adjacently hybridizing probes, under appropriate conditions, are ligated to one another to generate at least one ligation product. The ligation product thus comprises the target-specific portions. In certain embodiments, at least one probe in a probe set further comprises at least one hybridization tag, at least one primer-binding portion, at least one reporter group, or combinations thereof; and the ligation of such a probe set comprises the target-specific portions and at least one hybridization tag, at least one primer-binding portion, at least one reporter group, or combinations thereof, as appropriate. Those in the art will understand that, depending on the ligase and the reaction conditions, the at least one ligation product can but need not include at least one misligation product.

In certain embodiments, at least one ligation product comprising at least one primer-binding portion is combined with at least one primer and a polymerase to form an amplification reaction composition. In certain embodiments, the amplification reaction composition comprises at least one primer set. The amplification reaction composition is subjected to at least one cycle of amplification to generate at least one amplified ligation product. In certain embodiments, the target nucleic acid sequences are first amplified and then combined with at least one probe set to form a ligation reaction composition. Such ligation reaction compositions are subjected to at least one cycle of ligation, wherein adjacently hybridized probes, under appropriate conditions, are ligated together to form a ligation product. Those in the art will understand that, depending on the ligase and the reaction conditions, the at least one amplified ligation product can but need not include at least one amplified misligation product.

In certain embodiments, at least one first probe, at least one second probe, or at least one first probe and at least one second probe of a probe set further comprise at least one hybridization tag designed to allow hybridization with corresponding hybridization tag complements, such as capture oligonucleotides attached to a support; or to provide a unique molecular weight or length, or mobility, including without limitation, electrophoretic mobility, particularly when the hybridization tag comprises at least one mobility modifier. In certain embodiments, at least one probe further comprises, at least one reporter group, including without limitation at least one fluorescent reporter group and/or at least one affinity tag; at least one mobility modifier; at least part of at least one reporter probe binding portion; or combinations thereof.

In certain embodiments, at least one primer comprises at least one hybridization tag designed to allow hybridization with corresponding hybridization tag complements, such as capture oligonucleotides attached to a support; or to provide a unique molecular weight or length, or mobility, including without limitation, electrophoretic mobility, particularly when the hybridization tag comprises at least one mobility modifier. In certain embodiments, at least one primer further comprises at least one reporter group, including without limitation at least one fluorescent reporter group and/or at least one affinity tag; at least one mobility modifier; at least part of at least one reporter probe binding portion; or combinations thereof.

In certain embodiments, single-stranded amplification products comprising hybridization tags, suitable for hybridization with a support comprising corresponding hybridization tag complements, can be generated by several alternate methods including, without limitation, asymmetric PCR, asymmetric reamplification, nuclease digestion, and chemical denaturation. Detailed descriptions of such processes can be found, among other places, in Ausbel et al., Current Protocols in Molecular Biology (1993) including supplements through April 2004, John Wiley & Sons (hereinafter "Ausbel et al."), Novagen Strandase™ Kit insert, Sambrook et al., Molecular Cloning, A Laboratory Manual, Cold Spring Harbor Press (1989; hereinafter "Sambrook et al."), Little et al., J. Biol. Chem. 242:672 (1967) and PCT Publication No. WO 01/92579.

In certain embodiments, methods are disclosed for generating at least two ligation products, comprising: at least one step for interrogating at least one first target nucleotide; at least one step for interrogating at least one second target nucleotide; at least one step for generating at least one first ligation product; and at least one step for generating at least one second ligation product. Certain embodiments of these methods further comprise at least one step for amplifying at least one target nucleic acid sequence, at least one step for amplifying at least one ligation product; at least one step for digesting at least one amplified ligation product; at least one step for digesting the at least one ligation product; at least one step for amplifying at least one digested ligation product; or combinations thereof.

In certain embodiments, methods are disclosed for identifying at least one first and at least one second target nucleotide in a mixed population, comprising: at least one step for interrogating at least one first target nucleotide; at least one step for interrogating at least one second target nucleotide; at least one step for generating at least one first ligation product; at least one step for generating at least one second ligation product; and at least one step for identifying the at least one first and the at least one second target nucleotide. Certain embodiments of these methods further comprise at least one step for amplifying at least one target nucleotide; at least one step for amplifying at least one ligation product; at least one step for digesting at least one amplified ligation product; at least one step for digesting the at least one ligation product; at least one step for amplifying at least one digested ligation product; or combinations thereof.

Those skilled in the art will appreciate that the at least one step for interrogating can be performed using the probes and probe sets disclosed herein; that the at least one step for generating at least one ligation product can be performed using the ligation means and/or ligation techniques disclosed herein; that the at least one step for generating at least one amplified ligation product can be performed using the amplification means, amplification techniques, ligation means, and/or ligation techniques disclosed herein, including combinations thereof; that the at least one step for generating at least one target nucleotide can be performed using the amplification means and techniques disclosed herein; that the at least one step for generating at least one digested ligation product or at least one ligation product surrogate can be performed using the digesting means and/or digestion techniques disclosed herein; and that the at least one step for identifying at least one target nucleotide can be performed using the identifying and determining means and techniques disclosed herein. In certain embodiments, identifying can, but need not, comprise substeps for separating, detecting, evaluating, analyzing, comparing, or combinations thereof. In certain embodiments, the separating is performed independently, i.e., is not a substep of the identifying. Certain of the disclosed methods and kits comprise at least two separating steps or means for separating and can, but need not, include at least two separating techniques.

In certain embodiments, methods are disclosed for identifying at least one first target nucleotide and at least one second target nucleotide in a mixed population, comprising: at least one step for interrogating the at least one first target nucleotide, the at least one amplified first target nucleotide, the at least one second target nucleotide, the at least one amplified second target nucleotide, or combinations thereof; at least one step for generating at least one first ligation product, at least one second ligation product, or at least one first ligation product and at least one second ligation product; and at least one step for identifying the at least one first target nucleotide, the at least one second target nucleotide, or the at least one first target nucleotide and the at least one second target nucleotide in the mixed population. In certain embodiments, such methods further comprise at least one step for amplifying at least one first target nucleotide, at least one second target nucleotide, or at least one first target nucleotide and at least one second target nucleotide; at least one step for digesting at least one first ligation product, at least one first ligation product surrogate, at least one second ligation product, at least one second ligation product surrogate, or combinations thereof; or at least one such step for amplifying and at least one such step for digesting.

In certain embodiments, the first and the second ligation reaction compositions are formed in parallel. In certain embodiments, the first and the second ligation reaction compositions are formed separately. In certain embodiments, the first and the second ligation reaction compositions are subjected to at least one cycle of ligation in parallel. In certain embodiments, the first and the second ligation reaction compositions are subjected to at least one cycle of ligation separately. In certain embodiments, at least one cycle of ligation comprises a multiplicity of cycles of ligation.

In certain embodiments, at least one first ligation product, at least one second ligation product, or at least one first ligation product and at least one second ligation product, further comprise at least one primer-binding portion, at least one reporter group, at least one affinity tag, at least one mobility modifier, at least one hybridization tag, at least one reporter probe-binding portion, or combinations thereof. In certain embodiments, identifying comprises combining at least one reporter probe with at least one ligation product or its surrogate. In certain embodiments, identifying comprises at least one detecting step, such as detecting at least one reporter group on at least one ligation product or its surrogate or at least one reporter probe or at least part of a reporter probe, and at least one quantifying step, such as using a standard curve to extrapolate the amount of the target nucleotide in the sample based on at least one quantifiable ligation product parameter or by evaluating the ligation rate or ratio of at least two ligation products. In certain embodiments, at least one quantifying step comprises quantitative PCR. In certain embodiments, identifying comprises at least one mobility-dependent analytical technique, including without limitation capillary electrophoresis, at least one substrate, including without limitation, at least one microarray or at least one substrate comprising at least one affinity tag, or at least one mobility-dependent analytical technique and at least one substrate.

The instant teachings also provide kits designed to expedite performing the subject methods. Kits serve to expedite the performance of the disclosed methods by assembling two or more components required for carrying out the methods. In certain embodiments, kits contain components in pre-measured unit amounts to minimize the need for measurements by end-users. In certain embodiments, kits include instructions for performing one or more of the disclosed methods. In certain embodiments, kit components are optimized to operate in conjunction with one another.

The disclosed kits may be used to generate at least one ligation product, at least one amplified ligation product, at least one amplified digested ligation product, at least one digested ligation product, or combinations thereof. In certain embodiments, the instant kits comprise Afu ligase, at least one second ligase, at least one polymerase, at least one nuclease, at least one reporter group, at least one mobility modifier, at least one affinity tag, at least one hybridization tag, at least one probe set, at least one primer, or combinations thereof. In certain embodiments, the Afu ligase comprises at least one enzymatically active mutant of Afu ligase, at least one enzymatically active variant of Afu ligase, or combinations thereof. In certain embodiments, kits are disclosed that comprise at least one means for ligating, at least one means for amplifying, at least one means for separating, at least one means for digesting, at least one detection means, at least one identifying means, or combinations thereof.

DESCRIPTION OF EXEMPLARY EMBODIMENTS

Figure 1:
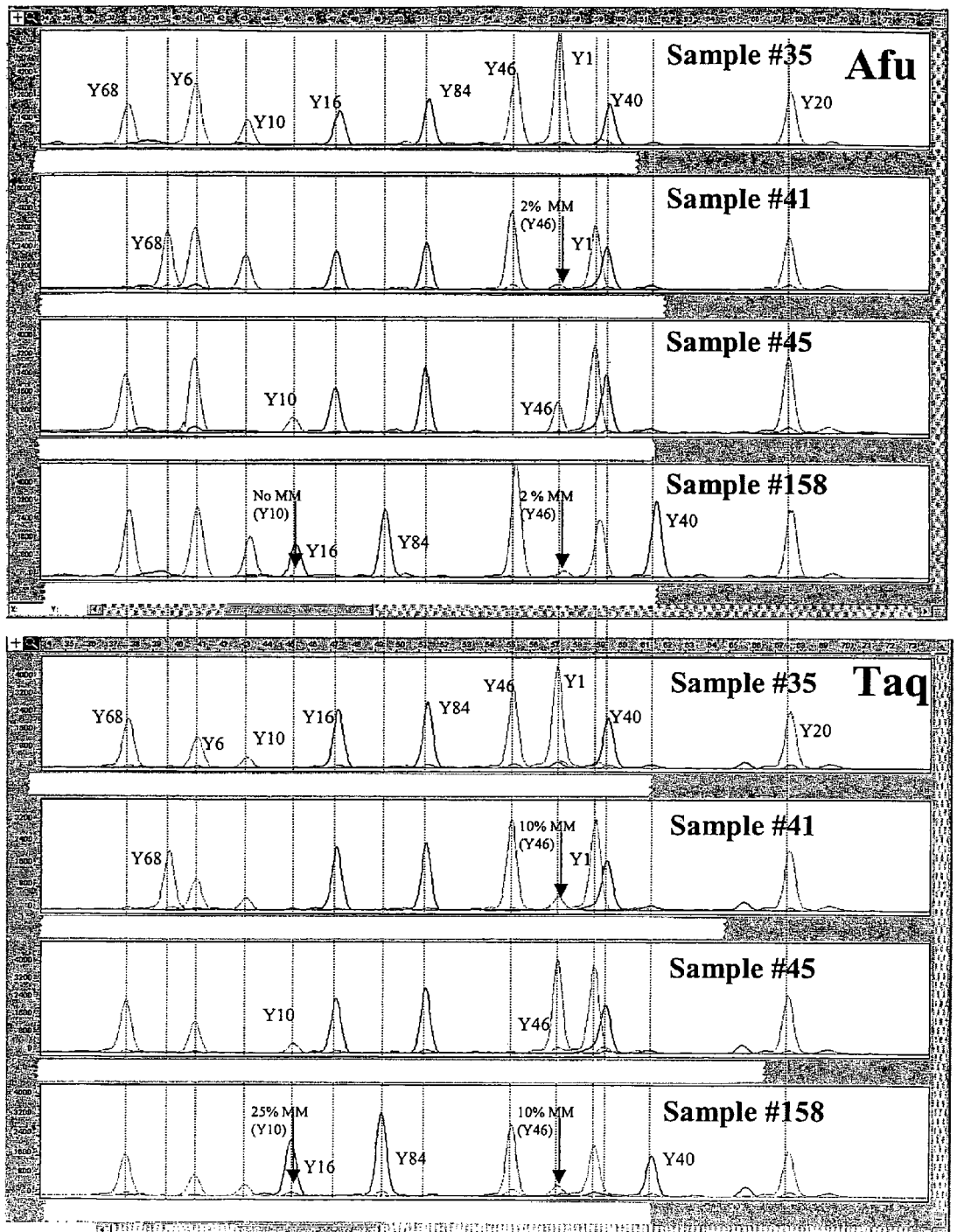
FIG. 1: depicts two panels of illustrative electropherograms, each showing ligation product peaks, including misligation product peaks, generated according to one of the disclosed methods using human gDNA target nucleic acid sequences (Sample # 35, 41, 45 and 158) and Y-chromosome SNP sites (e.g., Y1, Y6, Y10, Y16, Y20, Y40, Y46, Y68, and Y84), as described in Example 7. The top panel of four electropherograms shows the (mis)ligation product peaks obtained with each of the four samples using Afu ligase and the bottom panel of four electropherograms shows the (mis) ligation product peaks obtained with each of the four samples using Taq ligase. Peaks marked with an arrow and "% MM" indicate misligation product peaks and the percent of misligation product generated compared to the match ligation product. The x-axis (numbered across the top) represents size in nucleotide length relative to a LIZ 120 size standard and the y-axis represents fluorescent intensity in relative fluorescence units (RFU).

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. In the event that one or more of the incorporated literature and similar materials differs from or contradicts this application, including but not limited to defined terms, term usage, described techniques, or the like, this application controls.

I. Definitions

The term "adjacently hybridized oligonucleotides" refers to the final location of two nucleic acid sequences (typically oligonucleotide probes), relative to a target nucleic acid sequence or template prior to ligation, regardless of how they arrived at that final location. Under appropriate conditions, adjacently hybridized oligonucleotides can be ligated together to form a (mis)ligation product. In certain embodiments, two nucleic acid sequences hybridize in a juxtaposed fashion such that the 3'-end of the upstream oligonucleotide (relative to the template in a 3'-5' orientation, left to right) is on one side of a ligation junction, also referred to as a ligation site, and the 5'-end of the downstream probe is on the opposing end of the ligation junction. In certain embodiments, two probes of a probe set hybridize to the corresponding template but are not immediately adjacent. Before the two probes can be ligated together, an intermediate gap-filling step such a primer extension is be performed. In certain embodiments, a series of three or more oligonucleotides are ligated together on the template. In this context, the term oligonucleotide, such as an oligonucleotide probe can include a nucleic acid sequence with at least two linked nucleotides or at least one nucleotide linked to at least one adjacent nucleotide analog, wherein either the at least two nucleotide, the at least one analog, or both, can but need not be modified.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

The term "corresponding" as used herein refers to at least one specific relationship between the elements to which the term refers. For example, at least one first probe of a particular probe set corresponds to at least one second probe of the same probe set, and vice versa. At least one primer is designed to anneal with the primer-binding portion of at least one corresponding probe, at least one corresponding (mis)ligation product, at least one corresponding amplified (mis)ligation product, at least one corresponding digested (mis)ligation product, at least one corresponding digested amplified (mis)ligation product, or combinations thereof. The target-specific portions of the probes of a particular probe set are designed to hybridize with a complementary or substantially complementary region of the corresponding target nucleic acid sequence. A particular affinity tag binds to the corresponding affinity tag, for example but not limited to, biotin binding to streptavidin. A particular hybridization tag anneals with its corresponding hybridization tag complement; and so forth.

The term "enzymatically active mutants or variants thereof" and equivalent terms when used in reference to one or more enzyme, such as one or more polymerase, one or more ligase, one or more nuclease, or the like, refers to one or more polypeptide derived from the corresponding enzyme that retains at least some of the desired enzymatic activity, such as ligating, amplifying, or digesting, as appropriate. Also within the scope of this term are: enzymatically active fragments, including but not limited to, cleavage products, for example but not limited to Klenow fragment, Stoffel fragment, or recombinantly expressed fragments and/or polypeptides that are smaller in size than the corresponding enzyme; mutant forms of the corresponding enzyme, including but not limited to, naturally-occurring mutants, such as those that vary from the "wild-type" or consensus amino acid sequence, mutants that are generated using physical and/or chemical mutagens, and genetically engineered mutants, for example but not limited to random and site-directed mutagenesis techniques; amino acid insertions and deletions, and changes due to nucleic acid nonsense mutations, missense mutations, and frameshift mutations (see, e.g., Sriskanda and Shuman, Nucl. Acids Res. 26(2):525-31, 1998; Odell et al., Nucl. Acids Res. 31(17):5090-5100, 2003); reversibly modified nucleases, ligases, and polymerases, for example but not limited to those described in U.S. Pat. No. 5,773,258; biologically active polypeptides obtained from gene shuffling techniques (see, e.g., U.S. Pat. Nos. 6,319,714 and 6,159,688), splice variants, both naturally occurring and genetically engineered, provided that they are derived, at least in part, from one or more corresponding enzymes; polypeptides corresponding at least in part to one or more such enzymes that comprise modifications to one or more amino acids of the native sequence, including without limitation, adding, removing or altering glycosylation, disulfide bonds, hydroxyl side chains, and phosphate side chains, or crosslinking, provided such modified polypeptides retain at least some appropriate catalytic activity; and the like.

The skilled artisan will readily be able to measure enzymatic activity using an appropriate well-known assay. Thus, an appropriate assay for polymerase catalytic activity might include, for example, measuring the ability of a variant to incorporate, under appropriate conditions, rNTPs or dNTPs into a nascent polynucleotide strand in a template-dependent manner. Likewise, an appropriate assay for ligase catalytic activity might include, for example, the ability to ligate adjacently hybridized oligonucleotides comprising appropriate reactive groups, such as disclosed herein. Protocols for such assays may be found, among other places, in Sambrook et al., Sambrook and Russell, Molecular Cloning, Third Edition, Cold Spring Harbor Press (2000) (hereinafter "Sambrook and Russell"), Ausbel et al., and Housby and Southern, Nucl. Acids Res. 26:4259-66, 1998).

The terms "fluorophore" and "fluorescent reporter group" are intended to include any compound, label, or moiety that absorbs energy, typically from an illumination source or energy transfer, to reach an electronically excited state, and then emits energy, typically at a characteristic wavelength, to achieve a lower energy state. For example but without limitation, when certain fluorophores are illuminated by an energy source with an appropriate excitation wavelength, typically an incandescent or laser light source, photons in the fluorophore are emitted at a characteristic fluorescent emission wavelength. Fluorophores, sometimes referred to as fluorescent dyes, may typically be divided into families, such as fluorescein and its derivatives; rhodamine and its derivatives; cyanine and its derivatives; coumarin and its derivatives; Cascade Blue™ and its derivatives; Lucifer Yellow and its derivatives; BODIPY and its derivatives; and the like. Exemplary fluorophores include indocarbocyanine (C3), indodicarbocyanine (C5), Cy3, Cy3.5, Cy5, Cy5.5, Cy7, Texas Red, Pacific Blue, Oregon Green 488, Alexa Fluor 488, Alexa Fluor 532, Alexa Fluor 546, Alexa Fluor 568, Alexa Fluor 594, Alexa Fluor 647, Alexa Fluor 660, Alexa Fluor 680, JOE, Lissamine, Rhodamine Green, BODIPY, fluorescein isothiocyanate (FITC), carboxy-fluorescein (FAM), phycoerythrin, rhodamine, dichlororhodamine (dRhodamine™), carboxy tetramethylrhodamine (TAMRA™), carboxy-X-rhodamine (ROX™), LIZ™, VIC™, NED™, PET™, SYBR, PicoGreen, RiboGreen, and the like. Descriptions of fluorophores and their use, can be found in, among other places, R. Haugland, Handbook of Fluorescent Probes and Research Products, 9$^{th}$ ed. (2002), Molecular Probes, Eugene, Oreg. (hereinafter "Molecular Probes Handbook"); M. Schena, Microarray Analysis (2003), John Wiley & Sons, Hoboken, N.J.; Synthetic Medicinal Chemistry 2003/2004 Catalog, Berry and Associates, Ann Arbor, Mich.; U.S. Pat. No. 6,025,505; G. T. Hermanson, Bioconjugate Techniques, Academic Press, San Diego, Calif. (1996; hereinafter "Bioconjugate Techniques"); and Glen Research 2002 Catalog, Sterling, Va. Near-infrared dyes are expressly within the scope of the terms fluorophore and fluorescent reporter group, as are combination labels, such as combinatorial fluorescence energy transfer tags (see, e.g. Tong et al., Nat. Biotech. 19:756-59, 2001).

The term "hybridization tag" as used herein refers to an oligonucleotide sequence that can be used for separating the element (e.g., ligation products, surrogates, ZipChutes, etc.) of which it is a component or to which it is bound, including without limitation, bulk separation; for tethering or attaching the element to which it is bound to a substrate, which may or may not include separating; for annealing a hybridization tag complement that may comprise at least one moiety, such as a mobility modifier, one or more reporter groups, and the like; or combinations thereof. In certain embodiments, the same hybridization tag is used with a multiplicity of different elements to effect: bulk separation, substrate attachment, or combinations thereof. A "hybridization tag complement" typically refers to at least one oligonucleotide that comprises at least one sequence of nucleotides that are at least substantially complementary to and hybridize with the corresponding hybridization tag. In various embodiments, hybridization tag complements serve as capture moieties for attaching at least one hybridization tag:element complex to at least one substrate; serve as "pull-out" sequences for bulk separation procedures; or both as capture moieties and as pull-out sequences. In certain embodiments, at least one hybridization tag complement comprises at least one reporter group and serves as a label for at least one ligation product, at least one ligation product surrogate, or combinations thereof. In certain embodiments, identifying comprises detecting one or more reporter groups on or attached to at least one hybridization tag complement or at least part of a hybridization tag complement.

Typically, hybridization tags and their corresponding hybridization tag complements are selected to minimize: internal self-hybridization; cross-hybridization with different hybridization tag species, nucleotide sequences in a reaction composition, including but not limited to gDNA, different species of hybridization tag complements, target-specific portions of probes; and the like; but should be amenable to facile hybridization between the hybridization tag and its corresponding hybridization tag complement. Hybridization tag sequences and hybridization tag complement sequences can be selected by any suitable method, for example but not limited to, computer algorithms such as described in PCT Publication Nos. WO 96/12014 and WO 96/41011 and in European Publication No. EP 799,897; and the algorithm and parameters of SantaLucia (Proc. Natl. Acad. Sci. 95:1460-65 (1998)). Descriptions of hybridization tags can be found in, among other places, U.S. Pat. No. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides" therein); U.S. Pat. No. 5,935,793 (referred to as "identifier tags" therein); and PCT Publication No. WO 01/92579 (referred to as "addressable support-specific sequences" therein); and Gerry et al., J. Mol. Biol. 292:251-262 (1999; referred to as "zip-codes" and "zip-code complements" therein). Those in the art will appreciate that a hybridization tag and its corresponding hybridization tag complement are, by definition, complementary to each other and that the terms hybridization tag and hybridization tag complement are relative and can essentially be used interchangeably in most contexts.

Hybridization tags can be located on at least one end of at least one probe, at least one primer, at least one ligation product, at least one ligation product surrogate, or combinations thereof; or they can be located internally. In certain embodiments, at least one hybridization tag is attached to at least one probe, at least one primer, at least one ligation product, at least one ligation product surrogate, or combinations thereof, via at least one linker arm. In certain embodiments, at least one linker arm is cleavable.

In certain embodiments, hybridization tags are at least 12 bases in length, at least 15 bases in length, 12-60 bases in length, or 15-30 bases in length. In certain embodiments, at least one hybridization tag is 12, 15, 20, 21, 22, 23, 24, 25, 26, 27, 28, 29, 30, 45, or 60 bases in length. In certain embodiments, at least two hybridization tag:hybridization tag complement duplexes have melting temperatures that fall within a $\Delta T_m$ range ($T_{max}$-$T_{min}$) of no more than 10° C. of each other. In certain embodiments, at least two hybridization tag:hybridization tag complement duplexes have melting temperatures that fall within a $\Delta T_m$ range of 5° C. or less of each other.

In certain embodiments, at least one hybridization tag complement comprises at least one reporter group, at least one mobility modifier, at least one reporter probe binding portion, or combinations thereof. In certain embodiments, at least one hybridization tag complement is annealed to at least one corresponding hybridization tag and, subsequently, at least part of that hybridization tag complement is released and detected.

The term "ligation product" refers to a molecule that is generated when an internucleotide linkage is formed between two corresponding probes by the action of a ligase. Those in the art understand that, under certain conditions, such an internucleotide linkage can be formed between a pair of matched probes, a pair of mismatched probes (that is at least one of the two probes comprises at least one nucleotide or nucleotide analog that is mismatched with the corresponding template), or both. Thus, the term (mis)ligation is used herein to collectively refer to at least one match ligation, at least one mismatch ligation (sometimes referred to as misligation), or at least one match ligation and at least one misligation. Hence, by way of illustration, at least one "(mis)ligation product" refers to at least one ligation product, at least one misligation product, or at least one ligation product and at least one misligation product; at least one "(mis)ligation product surrogate" refers to at least one ligation product surrogate, at least one misligation product surrogate, or at least one ligation product surrogate and at least one misligation product surrogate; and so forth. The term "misligation" is generally intended to refer to products, surrogates, and the like that result from mismatch ligation reaction, but not match ligation reactions.

The term "ligation product surrogate" as used herein refers to any molecule or moiety whose detection or identification indicates the existence of one or more corresponding ligation products. A ligation product surrogate can, but need not, include at least part of the corresponding ligation product. Exemplary ligation product surrogates include but are not limited to, digested ligation products; amplified ligation products; digested amplified ligation products; one or more moieties cleaved or released from a ligation product or ligation product surrogate; one or more complementary strand or counterpart of a ligation product or ligation product surrogate; reporter probes; including but not limited to cleavage and amplification products thereof; hybridization tag complements, including but not limited to ZipChutes™ (typically a molecule or complex comprising at least one hybridization tag complement, at least one mobility modifier, and at least one reporter group, generally a fluorescent reporter group; Applied Biosystems, see, e.g., Applied Biosystems Part Number 4344467 Rev. C; see also U.S. Provisional Patent Application Ser. No. 60/517470); and the like. The term "digested amplified ligation product" is intended to include a ligation product that is digested then amplified as well as a ligation product that is amplified then digested. Likewise, the terms "misligation product surrogate" and "(mis)ligation product surrogate" have the meanings in reference to misligation products or (mis)ligation products respectively.

As used herein, "ligation rate" or "rate" are relative terms that are determined by evaluating at least one measurable parameter of at least one ligation product generated by a given ligase. In certain embodiments, a "ligation rate ratio" or "ratio" is obtained by comparing at least one quantifiable parameter of at least one ligation product generated by a first ligase with the same measurable parameter of the ligation product generated by a given second ligase under the same conditions, i.e., ligase 1/ligase 2, or vice versa, as appropriate. By way of illustration, without limitation, if the integrated area under the curve corresponding to exemplary ligation product A obtained using Afu ligase, as determined with an AB PRISM® 3100 Genetic Analyzer using GeneScan® Analysis Software (Applied Biosystems), is 10 and the integrated area under the curve corresponding to exemplary ligation product B obtained using Taq ligase under the same conditions is 1, the corresponding ligation rate ratio is 10:1 (Afu:Taq) or 1:10 (Taq:Afu). In certain embodiments, the ligation rate for a given ligation product is compared to at least one corresponding standard curve. Those in the art appreciate that numerous measurable parameters exist that can be used to compare the amount of ligation product generated by two ligases, including without limitation, ligation product peak height, integrated area under the curve for the ligation products, and so forth. By evaluating the ligation rate or the ligation rate ratio, one can identify and determine the quantity of at least one target nucleotide in a mixed population sample.

The term "mixed population" refers to a sample, or at least a multiplicity of target nucleic acid sequences, that contains or potentially contains nucleic acid sequences obtained or derived from at least two different donors, for example but not limited to, at least two humans; at least two cells that differ by at least one target nucleotide, including without limitation, a transformed or cancerous cell and a non-transformed cell or emerging drug-resistant mutant cells in cancer patients undergoing chemotherapy; at least two microorganisms that differ by at least one target nucleotide, including without limitation, two different species of the same or similar genus (for example but not limited to, *Streptococcus mutans* and *Streptococcus pyogenes*) two strains of the same species (e.g., *E. coli* and ETEC), emerging drug resistant mutants in patients undergoing antibiotic therapy; and two viruses that differ by at least one target nucleotide, including without limitation, different strains of the same virus such as emerging SARS coronavirus and influenza A strains, mutants (e.g. emerging drug-resistant HIV mutants in AIDS patients undergoing antiviral therapy). Exemplary sources for mixed population samples include: forensic specimens, such as those obtained at crime or mass fatality scenes; clinical specimens, such as blood, sputum, stool, tissue, swabs, biopsy material, etc.; epidemiologic, environmental samples, or bioterror monitoring samples including food, air (including without limitation samples obtained using air sampling devices or "sniffers"), and water samples; and the like. Expressly within the scope of mixed populations are amplified target nucleic acid sequences, regardless of whether they remain in the sample or are isolated.

The term "sample" is used in a broad sense and is intended to include a variety of biological materials that contain or potentially contain target nucleic acid sequences from at least two sources that are to be distinguished or identified. Exemplary biological samples include, but are not limited to, whole blood; red blood cells; white blood cells; buffy coat; swabs, including but not limited to buccal swabs, throat swabs, vaginal swabs, urethral swabs, cervical swabs, throat swabs, rectal swabs, lesion swabs, abcess swabs, nasopharyngeal swabs, and the like; urine; sputum; saliva; semen; lymphatic fluid; amniotic fluid; cerebrospinal fluid; peritoneal effusions; pleural effusions; fluid from cysts; synovial fluid; vitreous humor; aqueous humor; bursa fluid; eye washes; eye aspirates; plasma; serum; pulmonary lavage; lung aspirates; and tissues, including but not limited to, liver, spleen, kidney, lung, intestine, brain, heart, muscle, pancreas, and the like. The skilled artisan will appreciate that lysates, extracts, or material obtained from any of the above exemplary biological samples are also within the scope of the current teachings. Tissue culture cells, including explanted material, primary cells, secondary cell lines, and the like, as well as lysates, extracts, or materials obtained from any cells, are also within the meaning of the term sample as used herein. Microorganisms and viruses that may be present on or in a sample are also within the scope of the teachings herein. Materials obtained from forensic, epidemiologic, environmental and bio-monitoring settings and that contain target nucleic acid sequences are also within the intended meaning of the term sample.

The term "mobility-dependent analytical technique" as used herein refers to any means for separating different molecular species based on differential rates of migration of those different molecular species in one or more separation processes. Exemplary mobility-dependent analytical techniques include electrophoresis, chromatography, mass spectroscopy, sedimentation, e.g., gradient centrifugation, field-flow fractionation, multi-stage extraction techniques and the like. Descriptions of mobility-dependent analytical techniques can be found in, among other places, U.S. Pat. Nos. 5,470,705, 5,514,543, 5,580,732, 5,624,800, and 5,807,682; PCT Publication No. WO 01/92579; D. R. Baker, Capillary Electrophoresis, Wiley-Interscience (1995); Biochromatography: Theory and Practice, M. A. Vijayalakshmi, ed., Taylor & Francis, London, U.K. (2003); Krylov and Dovichi, Anal. Chem. 72:111 R-128R (2000); Swinney and Bornhop, Electrophoresis 21:1239-50 (2000); Crabtree et al., Electrophoresis 21:1329-35 (2000); and A. Pingoud et al., Biochemical Methods: A Concise Guide for Students and Researchers, Wiley-VCH Verlag GmbH, Weinheim, Germany (2002).

The term "mobility modifier" as used herein refers to at least one molecular entity, for example but not limited to, at least one polymer chain, that when added to at least one element (e.g., at least one probe, at least one primer, at least one ligation product, at least one ligation product surrogate, or combinations thereof affects the mobility of the element to which it is hybridized or bound, covalently or non-covalently, in at least one mobility-dependent analytical technique. Typically, a mobility modifier changes the charge/translational frictional drag when hybridized or bound to the element; or imparts a distinctive mobility, for example but not limited to, a distinctive elution characteristic in a chromatographic separation medium or a distinctive electrophoretic mobility in a sieving matrix or non-sieving matrix, when hybridized or bound to the corresponding element; or both (see, e.g., U.S. Pat. Nos. 5,470,705 and 5,514,543; Grossman et al., Nucl. Acids Res. 22:4527-34, 1994). In certain embodiments, a multiplicity of probes exclusive of mobility modifiers, a multiplicity of primers exclusive of mobility modifiers, a multiplicity of ligation products exclusive of mobility modifiers, a multiplicity of ligation product surrogates exclusive of mobility modifiers, or combinations thereof, have the same or substantially the same mobility in at least one mobility-dependent analytical technique.

In certain embodiments, a multiplicity of probes, a multiplicity of primers, a multiplicity of ligation products, a multiplicity of ligation product surrogates, or combinations thereof, have substantially similar distinctive mobilities, for example but not limited to, when a multiplicity of elements comprising mobility modifiers have substantially similar distinctive mobilities so they can be bulk separated or they can be separated from other elements comprising mobility modifiers with different distinctive mobilities. In certain embodiments, a multiplicity of probes comprising mobility modifiers, a multiplicity of primers comprising mobility modifiers, a multiplicity of ligation products comprising mobility modifiers, a multiplicity of ligation product surrogates comprising mobility modifiers, or combinations thereof, have different distinctive mobilities.

In certain embodiments, at least one mobility modifier comprises at least one nucleotide polymer chain, including without limitation, at least one oligonucleotide polymer chain, at least one polynucleotide polymer chain, or both at least one oligonucleotide polymer chain and at least one polynucleotide polymer chain. For example but not limited to, a series of additional non-target sequence-specific nucleotides in one or more probes such as "TTTT" or $[N]_x$, where "N" is any nucleotide and "x" is integer corresponding to the number of the particular nucleotide that is repeated (see, e.g., Tables 2 and 5); or nucleotide spacers (see e.g., Tong et al., Nat. Biotech. 19:756-759, 2001). In certain embodiments, at least one mobility modifier comprises at least one non-nucleotide polymer chain. Exemplary non-nucleotide polymer chains include, without limitation, peptides, polypeptides, polyethylene oxide (PEO), or the like. In certain embodiments, at least one polymer chain comprises at least one substantially uncharged, water-soluble chain, such as a chain composed of one or more PEO units; a polypeptide chain; or combinations thereof.

The polymer chain can comprise a homopolymer, a random copolymer, a block copolymer, or combinations thereof. Furthermore, the polymer chain can have a linear architecture, a comb architecture, a branched architecture, a dendritic architecture (including without limitation, polymers containing polyamidoamine branched polymers, Polysciences, Inc. Warrington, Pa.), or combinations thereof. In certain embodiments, at least one polymer chain is hydrophilic, or at least sufficiently hydrophilic when hybridized or bound to an element to ensure that the element-mobility modifier is readily soluble in aqueous medium. Where the mobility-dependent analytical technique is electrophoresis, in certain embodiments, the polymer chains are uncharged or have a charge/subunit density that is substantially less than that of its corresponding element.

The synthesis of polymer chains useful as mobility modifiers will depend, at least in part, on the nature of the polymer. Methods for preparing suitable polymers generally follow well-known polymer subunit synthesis methods. These methods, which may involve coupling of defined-size, multi-subunit polymer units to one another, either directly or through charged or uncharged linking groups, are generally applicable to a wide variety of polymers, such as PEO, polyglycolic acid, polylactic acid, polyurethane polymers, polypeptides, oligosaccharides, and nucleotide polymers. Such methods of polymer unit coupling are also suitable for synthesizing selected-length copolymers, e.g., copolymers of PEO units alternating with polypropylene units. Polypeptides of selected lengths and amino acid composition, either homopolymer or mixed polymer, can be synthesized by standard solid-phase methods (see, e.g., Int. J. Peptide Protein Res., 35: 161-214, 1990).

One method for preparing PEO polymer chains having a selected number of hexaethylene oxide (HEO) units, an HEO unit is protected at one end with dimethoxytrityl (DMT), and activated at its other end with methane sulfonate. The activated HEO is then reacted with a second DMT-protected HEO group to form a DMT-protected HEO dimer. This unit-addition is then carried out successively until a desired PEO chain length is achieved (see, e.g., U.S. Pat. No. 4,914,210; see also, U.S. Pat. No. 5,777,096).

The term "nucleotide base", as used herein, refers to a substituted or unsubstituted aromatic ring or rings. In certain embodiments, the aromatic ring or rings contain at least one nitrogen atom, such as a "nitrogenous base". In certain embodiments, the nucleotide base is capable of forming Watson-Crick and/or Hoogsteen hydrogen bonds with an appropriately complementary nucleotide base. Exemplary nucleotide bases and analogs thereof include, but are not limited to, naturally occurring nucleotide bases adenine, guanine, cytosine, 5 methyl-cytosine, uracil, thymine, and analogs of the naturally occurring nucleotide bases, including without limitation, 7-deazaadenine, 7-deazaguanine, 7-deaza-8-azaguanine, 7-deaza-8-azaadenine, N6-Δ2-isopentenyladenine (6iA), N6-Δ2-isopentenyl-2-methylthioadenine (2ms6iA), N2-dimethylguanine (dmG), 7-methylguanine (7 mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT published application WO 01/38584), ethenoadenine, indoles such as nitroindole and 4-methylindole, and pyrroles such as nitropyrrole. Certain exemplary nucleotide bases can be found, e.g., in Fasman, 1989, Practical Handbook of Biochemistry and Molecular Biology, pp. 385-394, CRC Press, Boca Raton, Fla., and the references cited therein.

The term "nucleotide", as used herein, refers to a compound comprising a nucleotide base linked to the C-1' carbon of a sugar, such as ribose, arabinose, xylose, and pyranose, and sugar analogs thereof. The term nucleotide also encompasses nucleotide analogs. The sugar may be substituted or unsubstituted. Substituted ribose sugars include, but are not limited to, those riboses in which one or more of the carbon atoms, for example the 2'-carbon atom, is substituted with one or more of the same or different, —R, —OR, —NR$_2$ azide, cyanide or halogen groups, where each R is independently H, $C_1$-$C_6$ alkyl, $C_2$-$C_7$ acyl, or $C_5$-$C_{14}$ aryl. Exemplary riboses include, but are not limited to, 2'-(C1-C6)alkoxyribose, 2'-(C5-C14)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C1-C6)alkylribose, 2'-deoxy-3'-(C1-C6)alkoxyribose and 2'-deoxy-3'-(C5-C14)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT published application nos. WO 98/22489, WO 98/39352; and WO 99/14226). Exemplary LNA sugar analogs within a polynucleotide include, but are not limited to, the structures:

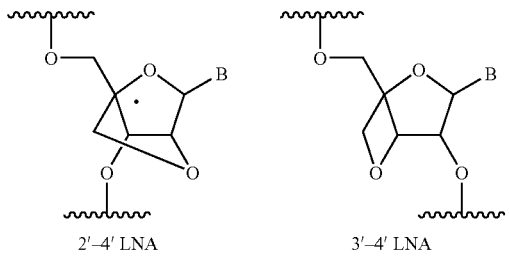

2'-4' LNA      3'-4' LNA where B is any nucleotide base.

Modifications at the 2'- or 3'-position of ribose include, but are not limited to, hydrogen, hydroxy, methoxy, ethoxy, allyloxy, isopropoxy, butoxy, isobutoxy, methoxyethyl, alkoxy, phenoxy, azido, cyano, amido, imido, amino, alkylamino, fluoro, chloro and bromo. Nucleotides include, but are not limited to, the natural D optical isomer, as well as the L optical isomer forms (see, e.g., Garbesi (1993) Nucl. Acids Res. 21:4159-65; Fujimori (1990) J. Amer. Chem. Soc. 112:7435; Urata, (1993) Nucleic Acids Symposium Ser. No. 29:69-70). When the nucleotide base is purine, e.g. A or G, the ribose sugar is attached to the $N^9$-position of the nucleotide base. When the nucleotide base is pyrimidine, e.g. C, T, or U, the pentose sugar is attached to the $N^1$-position of the nucleotide base, except for pseudouridines, in which the pentose sugar is attached to the $C^5$-position of the uracil nucleotide base (see, e.g., Kornberg and Baker, DNA Replication, $2^{nd}$ Ed., 1992, Freeman, San Francisco, Calif.).

One or more of the pentose carbons of a nucleotide may be substituted with a phosphate ester having the formula:

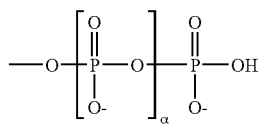

where α is an integer from 0 to 4. In certain embodiments, α is 2 and the phosphate ester is attached to the 3'- or 5'-carbon of the pentose. In certain embodiments, the nucleotides are those in which the nucleotide base is a purine, a 7-deazapurine, a pyrimidine, or an analog thereof. "Nucleotide 5'-triphosphate" refers to a nucleotide with a triphosphate ester group at the 5' position, and is sometimes denoted as "NTP", or "dNTP" and "ddNTP" to particularly point out the structural features of the ribose sugar. The triphosphate ester group may include sulfur substitutions for the various oxygens, e.g. α-thio-nucleotide 5'-triphosphates. Review of nucleotide chemistry can be found in, among other places, Shabarova, Z. and Bogdanov, A. Advanced Organic Chemistry of Nucleic Acids, VCH, New York, 1994; and Nucleic Acids in Chemistry and Biology, Blackburn and Gait, eds., Oxford University Press, New York, N.Y., 1996 (hereinafter "Blackburn and Gait").

The term "nucleotide analog", as used herein, refers to embodiments in which the pentose sugar and/or the nucleotide base and/or one or more of the phosphate esters of a nucleotide may be replaced with its respective analog. In certain embodiments, exemplary pentose sugar analogs are those described above. In certain embodiments, the nucleotide analogs have a nucleotide base analog as described above. In certain embodiments, exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., and may include associated counterions.

Also included within the definition of "nucleotide analog" are nucleotide analog monomers that can be polymerized into polynucleotide analogs in which the DNA/RNA phosphate ester and/or sugar phosphate ester backbone is replaced with a different type of internucleotide linkage. Exemplary polynucleotide analogs include, but are not limited to, peptide nucleic acids, in which the sugar phosphate backbone of the polynucleotide is replaced by a peptide backbone comprising at least one amide bond. See, e.g., Datar and Kim, Concepts in Applied Molecular Biology, Eaton Publishing, Westborough, Mass., 2003, particularly at pages 74-75; Verma and Eckstein, Ann. Rev. Biochem. 67:99-134, 1998; Goodchild, Bioconj. Chem., 1:165-187, 1990.

As used herein, the terms "polynucleotide", "oligonucleotide", "nucleic acid", and "nucleic acid sequence" are generally used interchangeably and mean single-stranded and double-stranded polymers of nucleotide monomers, including 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, tetraalkylammonium, $Mg^{2+}$, $Na^+$ and the like. A nucleic acid may be composed entirely of deoxyribonucleotides, entirely of ribonucleotides, or chimeric mixtures thereof. The nucleotide monomer units may comprise any of the nucleotides described herein, including, but not limited to, naturally occurring nucleotides and nucleotide analogs. Nucleic acids typically range in size from a few monomeric units, e.g. 5-40 when they are sometimes referred to in the art as oligonucleotides, to several thousands of monomeric nucleotide units. Nucleic acid sequence are shown in the 5' to 3' orientation from left to right, unless otherwise apparent from the context or expressly indicated differently; and in DNA, "A" denotes deoxyadenosine, "C" denotes deoxycytidine, "G" denotes deoxyguanosine, "T" denotes thymidine; while in RNA, "A" denotes adenosine, "C" denotes cytidine, "G" denotes guanosine, and "U" denotes uridine.

Nucleic acids include, but are not limited to, gDNA, cDNA, hnRNA, mRNA, rRNA, tRNA, fragmented nuleic acid, nucleic acid obtained from subcellular organelles such as mitochondria or chloroplasts, and nucleic acid obtained from microorganisms or DNA or RNA viruses that may be present on or in a biological sample.

Nucleic acids may be composed of a single type of sugar moiety, e.g., as in the case of RNA and DNA, or mixtures of different sugar moieties, e.g., as in the case of RNA/DNA chimeras. In certain embodiments, nucleic acids are ribopolynucleotides and 2'-deocyribopolynucleoties according to the structural formulae below:

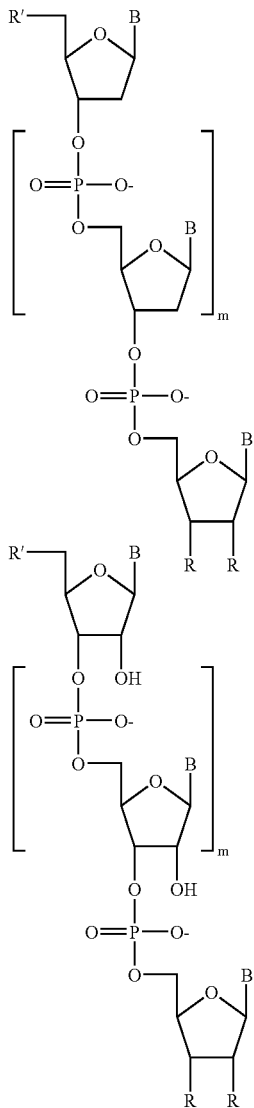

wherein each "B" is independently the base moiety of a nucleotide, e.g., a purine, a 7-deazapurine, a purine or purine analog substituted with one or more substituted hydrocarbons, a pyrimidine, a pyrimidine or pyrimidine analog substituted with one or more substituted hydrocarbons, or an analog nucleotide; each "m" defines the length of the respective nucleic acid and can range from zero to thousands, tens of thousands, or even more; each "R" is independently selected from the group comprising hydrogen, halogen, —R", —OR", and —NR"R", where each R" is independently (C1-C6) alkyl, (C2-C7) acyl or (C5-C14) aryl, cyanide, azide, or two adjacent Rs are taken together to form a bond such that the ribose sugar is 2',3'-didehydroribose; and each "R'" is independently hydroxyl or

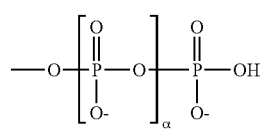

where α is zero, one or two.

In certain embodiments of the ribopolynucleotides and 2'-deoxyribopolynucleotides illustrated above, the nucleotide bases B are covalently attached to the C1' carbon of the sugar moiety as previously described.

The terms "nucleic acid", "nucleic acid sequence", "polynucleotide", and "oligonucleotide" can also include nucleic acid analogs, polynucleotide analogs, and oligonucleotide analogs. The terms "nucleic acid analog", "polynucleotide analog" and "oligonucleotide analog" are generally used interchangeably and, as used herein, refer to a nucleic acid that contains at least one nucleotide analog and/or at least one phosphate ester analog and/or at least one pentose sugar analog. Also included within the definition of nucleic acid analogs are nucleic acids in which the phosphate ester and/or sugar phosphate ester linkages are replaced with other types of linkages, such as N-(2-aminoethyl)-glycine amides and other amides (see, e.g., Nielsen et al., 1991, Science 254: 1497-1500; WO 92/20702; U.S. Pat. No. 5,719,262; U.S. Pat. No. 5,698,685;); morpholinos (see, e.g., U.S. Pat. No. 5,698, 685; U.S. Pat. No. 5,378,841; U.S. Pat. No. 5,185,144); carbamates (see, e.g., Stirchak & Summerton, 1987, J. Org. Chem. 52: 4202); methylene(methylimino) (see, e.g., Vasseur et al., 1992, J. Am. Chem. Soc. 114: 4006); 3'-thioformacetals (see, e.g., Jones et al., 1993, J. Org. Chem. 58: 2983); sulfamates (see, e.g., U.S. Pat. No. 5,470,967); 2-aminoethylglycine, commonly referred to as PNA (see, e.g., Buchardt, WO 92/20702; Nielsen (1991) Science 254:1497-1500); and others (see, e.g., U.S. Pat. No. 5,817,781; Frier & Altman, 1997, Nucl. Acids Res. 25:4429 and the references cited therein). Phosphate ester analogs include, but are not limited to, (i) $C_1$-$C_4$ alkylphosphonate, e.g. methylphosphonate; (ii) phosphoramidate; (iii) $C_1$-$C_6$ alkyl-phosphotriester; (iv) phosphorothioate; and (v) phosphorodithioate. See also, Scheit, Nucleotide Analogs, John Wiley, New York, (1980); Englisch, Angew. Chem. Int. Ed. Engl. 30:613-29, 1991; Agarwal, Protocols for Polynucleotides and Analogs, Humana Press, 1994; and S. Verma and F. Eckstein, Ann. Rev. Biochem. 67:99-134, 1999.

The term "performed in parallel" refers to doing the same or similar action at the same time or doing the same or similar actions twice in substantially the same time, typically within seconds or minutes of each other. For example, forming a first ligation reaction composition is performed in parallel with forming a second ligation reaction composition when the two ligation reaction compositions are formed at the same time, such as sub steps of the same act, or within minutes of each other. By way of example but without limitation, sequentially pipetting an aliquot of sample into each of a series of parallel sets of tubes is done in parallel if no substantial period of time elapses between each pipetting. The term "performed separately" refers to doing the same or similar act at different times, for example in the morning versus the afternoon, or on different days. By way of example but without limitation, if a first ligation reaction composition is subjected to at least one cycle of ligation in the morning of day one and a second ligation reaction composition is subjected to at least one cycle of ligation on the afternoon of day three, the two cycles of ligation were performed separately.

The term "polymerase" is used in a broad sense herein and includes amplifying means such as DNA polymerases, enzymes that typically synthesize DNA by incorporating deoxyribonucleotide triphosphates or analogs in the 5'=>3' direction in a template-dependent and primer-dependent manner; RNA polymerases, enzymes that typically synthesize RNA by incorporating ribonucleotide triphosphates or analogs, generally in a template-dependent manner; and reverse transcriptases, also known as RNA-dependent DNA polymerases, that synthesize DNA by incorporating deoxyribonucleotide triphosphates or analogs in the 5'=>3' direction in primer-dependent manner, typically using an RNA template. Descriptions of polymerases can be found in, among other places, R. M. Twyman, Advanced Molecular Biology, Bios Scientific Publishers Ltd. (1999); Polymerase Enzyme Resource Guide, Promega, Madison, Wis. (1998); P. C. Turner et al., Instant Notes in Molecular Biology, Bios Scientific Publishers Ltd. (1997); and B. D. Hames et al., Instant Notes in Biochemistry, Bios Scientific Publishers Ltd. (1997).

The term "primer" as used herein refers to an oligonucleotide comprising at least one region that is complementary or substantially complementary to the primer-binding portion of at least one probe, at least one (mis)ligation product, at least one (mis)ligation product surrogate, or combinations thereof, including sequences that are complementary to any of these, and that can anneal with such primer-binding portions or their complement under appropriate conditions. Primers typically serve as initiation sites for certain amplification techniques, including but not limited to, primer extension and PCR. A primer that hybridizes with a multiplicity of different probe species, (mis)ligation product species, (mis)ligation product surrogate species, or combinations thereof, is referred to as a "universal primer". In certain embodiments, at least one primer comprises at least one additional component, including but not limited to, at least one primer-binding portion, at least one reporter probe-binding portion, at least one reporter group, at least one hybridization tag, at least one mobility modifier, at least one affinity tag, or combinations thereof.

The criteria for designing sequence-specific primers and probes are well known to persons of ordinary skill in the art. Detailed descriptions of probe and primer design that provide for sequence-specific annealing can be found in, among other places, Diffenbach and Dveksler, PCR Primer, A Laboratory Manual, Cold Spring Harbor Press, 1995; Blackburn and Gait; and Kwok et al., Nucl. Acids Res. 18:999-1005, 1990; as well as numerous probe and primer design software programs.

The term "probe" as used herein, refers to an oligonucleotide comprising a target-specific portion that is capable, under appropriate conditions, of hybridizing with at least a part of at least one corresponding target nucleic acid sequence, including without limitation at least one amplified target nucleic acid sequence or the complement of at least one target nucleic acid sequence. A probe may include Watson-Crick bases, analogs, or modified bases, including but not limited to, the AEGIS bases (from Eragen Biosciences), described, e.g., in U.S. Pat. Nos. 5,432,272; 5,965,364; and 6,001,983. Additionally, bases may be joined by a natural phosphodiester bond or a different chemical linkage. Different chemical linkages include, but are not limited to, at least one amide linkage or at least one Locked Nucleic Acid (LNA) linkage, described in, e.g., published PCT Application Nos. WO 00/56748 and WO 00/66604.

Probes typically are part of at least one ligation probe set comprising at least one first probe and at least one second probe, that typically can be ligated or misligated, depending on the circumstances. In certain embodiments, at least one probe comprises at least one mismatched nucleotide relative to at least one portion of its corresponding target nucleic acid sequence. In certain embodiments, at least one mismatched nucleotide is at the 3'-end of the upstream probe, the 5'-end of the downstream probe, or both. In certain embodiments, at least one probe further comprises at least one reporter group, at least one affinity tag, at least one hybridization tag, at least one mobility modifier, at least one primer-binding portion, at least one reporter probe-binding portion, or combinations thereof. The target-specific portions and, when present, the primer-binding and/or reporter probe-binding portions, of the probes are of sufficient length to permit specific annealing with complementary sequences in the template, primers, or reporter probes, as appropriate.

As used herein, a "probe set" comprises at least one first probe and at least one corresponding second probe that are designed to hybridize with the corresponding template. Some probe sets may comprise more than one first probe or more than one second probe or both, to aid in interrogating one or more target nucleotide. In a typical probe set there is a single species of first probe and at least two species of second probe, or vice versa. For example, certain OLA protocols utilize a single species of downstream ligation probe (sometimes referred to as a locus specific oligonucleotide (LSO), a reporter probe, or a common probe) and at least two species of upstream ligation probe (sometimes referred to as allele specific oligonucleotides (ASOs) or wild type and mutant probes/primers) for each SNP site (including without limitation mitochondrial SNPs) or target nucleotide being interrogated (see, e.g., Landegren et al., Science 241:1077-80, 1988; Edelstein et al., J. Clin. Micro. 36(2):569-72, 1998; Shi, Clin. Chem. 47(2): 164-72, 2001). When the first probe and a second probe from a probe set are hybridized to the corresponding template, under appropriate conditions and in the presence or an appropriate ligase, the two probes are ligated together to generate a ligation product, provided that they comprise appropriate reactive groups, for example without limitation, a free 3' hydroxyl group on the upstream probe and a 5' phosphate group on the downstream probe. In certain embodiments, the first and a corresponding second probe hybridize adjacently, while in other embodiments, after the probes hybridize an intervening gap-filling step renders the 3'-end of the upstream probe adjacent to the 5-end of the downstream probe. In certain embodiments, only some of the probes from a probe set are combined with a first ligase, while at least some other probes from the same probe set are combined with a second ligase. For example without limitation, an illustrative probe set has two upstream probes (A and B) and one downstream probe (C); probes A and C are combined with a first ligase in a first ligation reaction composition and probes B and C are combined with a second ligase in a second ligase reaction composition.

In certain embodiments, the first probes and second probes in a probe set are designed with similar melting temperatures ($T_m$). Where a probe includes a complement of the target nucleotide being interrogated (sometimes referred to as a "pivotal complement"), preferably, the $T_m$ for the probe(s) comprising the complement(s) of the target nucleotide will be approximately 4-60° C. lower than the other probe(s) in the probe set that do not contain the target nucleotide complement. The probe comprising the pivotal complement will also preferably be designed with a $T_m$ near the ligation temperature. Thus, a probe with a mismatched nucleotide will more readily dissociate from the target at the ligation temperature. The ligation temperature, therefore, provides another way to discriminate between, for example, multiple potential alleles at a SNP site or alternative target nucleotides.

A mismatched base at the pivotal complement, however, may interfere with ligation since, absent misligation, it can't base pair with the SNP site nucleotide or the target nucleotide, even if both probes are otherwise fully hybridized to their respective target regions. Thus, highly related sequences that differ by as little as a single nucleotide can be distinguished, for example but not limited to, the alternative alleles at a SNP site, a single nucleotide mutation in a tumor repressor gene, such as p53, or a drug resistance mutation in a drug-resistant mutant microorganism or virus, such a point mutation in HIV protease from a patient being treated with one or more protease inhibitors, or the like; provided that misligation products are either not generated in detectable levels or do not become problematic. In certain embodiments, the pivotal complement is present at the 3'-end of the upstream probe, the 5'-end of the downstream probe, or both. In certain embodiments, the pivotal complement is not at the end of either the upstream probe or the downstream probe. For example without limitation, the pivotal complement can be the 3' penultimate nucleotide on the upstream probe.

Those in the art understand that probes and probe sets that are suitable for use with the disclosed methods and kits can be identified empirically using the current teachings and routine methods known in the art, without undue experimentation. For example, suitable probes and probe sets can be obtained by selecting appropriate target nucleotides and target nucleotide sequences by searching relevant scientific literature, including but not limited to appropriate databases, that list or identify known SNPs, mutations, including but not limited to drug-induced mutations, chromosomal translocations, and the like; or by experimental analysis. When target nucleic acid sequences of interest are identified, test probes can be synthesized and modified if desired, using well known oligonucleotide synthesis and organic chemistry techniques (see, e.g., Current Protocols in Nucleic Acid Chemistry, Beaucage et al., eds., John Wiley & Sons, New York, N.Y., including updates through April 2004 (hereinafter "Beaucage et al."); Blackburn and Gait; Glen Research 2002 Catalog, Sterling, Va.; and Synthetic Medicinal Chemistry 2003/2004, Berry and Associates, Dexter, Mich.). Test probes and/or probe sets are employed in the disclosed assays using appropriate target sequences and their suitability for interrogating the target nucleotide is evaluated. Standard curves can be generated, if desired, using pre-determined mixtures or serial dilutions of synthetic templates or gDNA as the target nucleic acid sequences in one or more of the disclosed ligation assays under standard conditions, as well known in the art (see, e.g., Overholtzer et al., Proc. Natl. Acad. Sci. 100:11547-52, 2002).

The term "reporter group" is used in a broad sense herein and refers to any identifiable tag, label, or moiety. The skilled artisan will appreciate that many different species of reporter groups can be used in the present teachings, either individually or in combination with one or more different reporter group. Exemplary reporter groups include, but are not limited to, fluorophores, radioisotopes, chromogens, enzymes, antigens including but not limited to epitope tags, heavy metals, dyes, phosphorescence groups, chemiluminescent groups, electrochemical detection moieties, affinity tags, binding proteins, phosphors, rare earth chelates, near-infrared dyes, including but not limited to, "Cy.7.SPh.NCS," "Cy.7.OphEt.NCS," "Cy7.OphEt.CO$_2$Su", and IRD800 (see, e.g., J. Flanagan et al., Bioconjug. Chem. 8:751-56 (1997); and DNA Synthesis with IRD800 Phosphoramidite, LI-COR Bulletin #111, LI-COR, Inc., Lincoln, Nebr.), electrochemiluminescence labels, including but not limited to, tris(bipyridal) ruthenium (II), also known as $Ru(bpy)_3^{2+}$, $Os(1,10$-phenanthroline)$_2$bis(diphenylphosphino)ethane$^{2+}$, also known as $Os(phen)_2(dppene)^{2+}$, luminol/hydrogen peroxide, Al(hydroxyquinoline-5-sulfonic acid), 9,10-diphenylanthracene-2-sulfonate, and tris(4-vinyl-4'-methyl-2,2'-bipyridal) ruthenium (II), also known as $Ru(v\text{-}bpy)_3^{2+}$), and the like.

The term reporter group also includes at least one element of multi-element reporter systems, e.g., affinity tags such as biotin/avidin, antibody/antigen, ligand/receptor including but not limited to binding proteins and their ligands, enzyme/substrate, and the like, in which one element interacts with other elements of the system in order to effect the potential for a detectable signal. Exemplary multi-element reporter systems include an oligonucleotide comprising at least one biotin reporter group and a streptavidin-conjugated fluorophore, or vice versa; an oligonucleotide comprising at least one dinitrophenyl (DNP) reporter group and a fluorophore-labeled anti-DNP antibody; and the like. In certain embodiments, reporter groups, particularly multi-element reporter groups, are not necessarily used for detection, but rather serve as affinity tags for separating, for example but not limited to, a biotin reporter group and a streptavidin coated substrate, or vice versa; a digoxygenin reporter group and an anti-digoxygenin antibody or a digoxygenin-binding aptamer; a DNP reporter group and an anti-DNP antibody or a DNP-binding aptamer; and the like. Detailed protocols for attaching reporter groups to oligonucleotides, polynucleotides, peptides, proteins, mono-, di- and oligosaccharides, organic molecules, and the like can be found in, among other places, Bioconjugate Techniques; Beaucage et al.; Molecular Probes Handbook; and Pierce Applications Handbook and Catalog 2003-2004, Pierce Biotechnology, Rockford, Ill. (2003; hereinafter "Pierce Applications Handbook").

In certain embodiments, at least one reporter group comprises at least one electrochemiluminescent moiety that can, under appropriate conditions, emit detectable electrogenerated chemiluminescence (ECL). In ECL, excitation of the electrochemiluminescent moiety is electrochemically driven and the chemiluminescent emission can be optically detected. Exemplary electrochemiluminescent reporter group species include: $Ru(bpy)_3^{2+}$ and $Ru(v\text{-}bpy)_3^{2+}$ with emission wavelengths of 620 nm; $Os(phen)_2(dppene)^{2+}$ with an emission wavelength of 584 nm; luminol/hydrogen peroxide with an emission wavelength of 425 nm; Al(hydroxyquinoline-5-sulfonic acid) with an emission wavelength of 499 nm; and 9,10-diphenylanothracene-2-sulfonate with an emission wavelength of 428 nm; and the like. Modified forms of these three electrochemiluminescent reporter group species that are amenable to incorporation into probes and coded molecular tags are commercially available or can be synthesized without undue experimentation using techniques known in the art. For example, a $Ru(bpy)_3^{2+}$ N-hydroxy succinimide ester for coupling to nucleic acid sequences through an amino linker group has been described (see, U.S. Pat. No. 6,048,687); and succinimide esters of $Os(phen)_2(dppene)^{2+}$ and $Al(HQS)_3^{3+}$ can be synthesized and attached to nucleic acid sequences using similar methods. The Ru(bpy)$_3^{2+}$ electrochemiluminescent reporter group can be synthetically incorporated into nucleic acid sequences using commercially available ru-phosphoramidite (IGEN International, Inc., Gaithersburg, Md.).

Additionally other polyaromatic compounds and chelates of ruthenium, osmium, platinum, palladium, and other transition metals have shown electrochemiluminescent properties. Detailed descriptions of ECL and electrochemiluminescent moieties can be found in, among other places, A. Bard and L. Faulkner, Electrochemical Methods, John Wiley & Sons (2001); M. Collinson and M. Wightman, Anal. Chem. 65:2576 et seq. (1993); D. Brunce and M. Richter, Anal. Chem. 74:3157 et seq. (2002); A. Knight, Trends in Anal. Chem. 18:47 et seq. (1999); B. Muegge et al., Anal. Chem. 75:1102 et seq. (2003); H. Abrunda et al., J. Amer. Chem. Soc. 104:2641 et seq. (1982); K. Maness et al., J. Amer. Chem. Soc. 118:10609 et seq. (1996); M. Collinson and R. Wightman, Science 268:1883 et seq. (1995); and U.S. Pat. No. 6,479,233.

The term "target nucleic acid sequence" as used herein refers to a specific nucleic acid oligomer, typically gDNA or a synthetic template, that contains one or more target nucleotides. A target nucleotide is that nucleotide in the target nucleic acid sequence that is interrogated by one or more probes of one or more probe sets to determine its identity. Thus, a first target nucleotide is present in the first target nucleic acid sequence, a second target nucleotide is present in the second target nucleic acid sequence, and so forth. Those in the art understand that a particular target nucleic acid sequence may, but need not, comprise more than one target nucleotide. While the target nucleic acid sequence is generally described as a single-stranded molecule, it is to be understood that double-stranded molecules that contain one or more target nucleotides are also considered target nucleic acid sequences. Target nucleic acid sequences can serve as hybridization templates on which corresponding ligation probes can anneal. The amplification product of all or part of a nucleic acid sequence can also typically serve as a hybridization template on which corresponding probes can anneal. Such amplified sequences are within the intended scope of the term target nucleic acid sequence, unless otherwise apparent from the context or expressly excluded.

Those in the art will appreciate that the complement of the disclosed probe, target, and primer sequences, or combinations thereof, may also be employed in the methods herein. For example without limitation, a gDNA sample comprises both the target nucleic acid sequence and its complement. Thus when a genomic sample is denatured, both the target nucleic acid sequence and its complement are present in the sample as single stranded sequences. The probes described herein or their complement will specifically hybridize to the appropriate sequence, either the target nucleic acid sequences or its complement.

II. Techniques

A target nucleic acid sequence according to the present teachings may be derived from any living, or once living, organism, including but not limited to, prokaryotes, archaea, viruses, and eukaryotes. The target nucleic acid may originate from the nucleus, typically gDNA, or may be extranuclear, e.g., plasmid, mitochondrial, viral, etc. The skilled artisan appreciates that gDNA includes not only full length material, but also fragments generated by any number of means, for example but not limited to, enzyme digestion, sonication, shear force, and the like, and that all such material, whether full length or fragmented, represent forms of target nucleic acid sequences.

A target nucleic acid sequence can be either synthetic or naturally occurring. Target nucleic acid sequences can be synthesized using oligonucleotide synthesis methods, and where appropriate, phosphorylation methods that are well-known in the art. Detailed descriptions of such techniques can be found in, among other places, Beaucage et al.; and Blackburn and Gait. Automated DNA synthesizers useful for synthesizing target nucleic acid sequences, probes, and primers are commercially available from numerous sources, including for example, the Applied Biosystems DNA Synthesizer Models 381A, 391, 392, and 394 (Applied Biosystems, Foster City, Calif.). Target nucleic acid sequences can also be generated biosynthetically, using in vivo methodologies and/or in vitro methodologies that are well known in the art. Descriptions of such technologies can be found in, among other places, Molecular Cloning: A Laboratory Manual, Sambrook et al., eds., Cold Spring Harbor Press, Cold Spring Harbor, N.Y., 2001 ("Sambrook et al."); and Ausbel et al.

A variety of methods are available for obtaining a naturally occurring target nucleic acid sequences for use with the current teachings. Purified or partially purified nucleic acid is commercially available from numerous sources, including among others, Coriell Cell Repositories, Coriell Institute for Medical Research, Camden, N.J.; and the American Type Culture Collection (ATCC), Manassas, Va. When the target nucleic acid sequence is obtained through isolation from a biological matrix, preferred isolation techniques include (1) organic extraction followed by ethanol precipitation, e.g., using a phenol/chloroform organic reagent (see, e.g., Sambrook et al.; Ausbel et al.), for example using an automated DNA extractor, e.g., the Model 341 DNA Extractor available from Applied Biosystems (Foster City, Calif.); (2) stationary phase adsorption methods (e.g., Boom et al., U.S. Pat. No. 5,234,809; Walsh et al., Biotechniques 10(4): 506-513, 1991); and (3) salt-induced DNA precipitation methods (see, e.g., Miller et al., Nucl. Acids Res. 16(3): 9-10, 1988), such precipitation methods being typically referred to as "salting-out" methods. Optimally, each of the above isolation methods is preceded by an enzyme digestion step to help eliminate unwanted protein from the sample, e.g., digestion with proteinase K, or other like proteases; a detergent step, or both (see, e.g., U.S. Patent Application Publication 2002/0177139; and U.S. patent application Ser. No. 10/618493). Commercially available nucleic acid extraction systems include, among others, the ABI PRISM® 6100 Nucleic Acid PrepStation and the ABI PRISM® 6700 Nucleic Acid Automated Work Station; nucleic acid sample preparation reagents and kits are also commercially available, including without limitation, NucPrep™ Chemistry, BloodPrep™ Chemistry, the ABI PRISM® TransPrep System, and PrepMan™ Ultra Sample Preparation Reagent (all from Applied Biosystems).

Ligation according to the present teachings comprises any enzymatic or non-enzymatic means wherein an inter-nucleotide linkage is formed between the opposing ends of nucleic acid probes that are adjacently hybridized on a target nucleic acid sequence to generate a (mis)ligation product. In certain embodiments, ligation also comprises at least one gap-filling procedure, wherein the ends of the two probes are not adjacently hybridized initially but the 3'-end of the upstream probe is extended by one or more nucleotide until it is adjacent to the 5'-end of the downstream probe, typically by a polymerase (see, e.g., U.S. Pat. No. 6,004,826). Exemplary ligases include without limitation, T4 DNA ligase, T4 RNA ligase, *Thermus thermophilus* (Tth) ligase, *Thermus aquati-*

*cus* (Taq) DNA ligase, *Thermus scotoductus* (Tsc) ligase, TS2126 (a thermophilic phage that infects Tsc) RNA ligase, *Archaeoglobus flugidus* (Afu) ligase, *Pyrococcus furiosus* (Pfu) ligase, *Thermococcus kodakaraensis* KOD1 ligase (lig$_{Tk}$), *Rhodothermus marinus* (Rm) ligase, *Methanobacterium thermoautotrophicum* (Mth) ligase, *Aquifex aeolicus* (Aae) ligase, *Aeropyrum pernix* K1 (Ape) ligase, or the like, including but not limited to reversibly inactivated ligases (see, e.g., U.S. Pat. No. 5,773,258), and enzymatically active mutants or variants thereof.

Ligation generally comprises at least one cycle of ligation, i.e., the sequential procedures of: hybridizing the target-specific portions of a first probe and a corresponding second probe to their respective complementary regions on the corresponding target nucleic acid sequences; ligating the 3' end of the upstream probe with the 5' end of the downstream probe to generate a ligation product; and denaturing the nucleic acid duplex to release the ligation product from the ligation product:target nucleic acid sequence duplex. The ligation cycle may or may not be repeated, for example, without limitation, by thermocycling the ligation reaction to amplify the (mis)ligation product using ligation probes, e.g., LDR, as distinct from using primers and polymerase to generate amplified (mis)ligation products, e.g., LCR (see, e.g., Cao, Trends in Biotech, 22(1):38-44, 2004).

Also within the scope of the teachings are ligation techniques such as gap-filling ligation, including, without limitation, gap-filling OLA, LDR, and LCR, bridging oligonucleotide ligation, and correction ligation. Descriptions of these techniques can be found in, among other places, U.S. Pat. Nos. 5,185,243 and 6,004,826; published European Patent Applications EP 320308 and EP 439182; and PCT Publication Nos. WO 90/01069 and WO 01/57268.

When used in the context of the present teachings, "suitable for ligation" refers to at least one first probe and at least one corresponding second probe, wherein each probe comprises an appropriately reactive group, typically a free hydroxyl group on the 3' end of the upstream probe and a free phosphate group on the 5' end of the downstream probe. Under appropriate conditions, phosphodiester bond formation between the 3'-hydroxyl group and the adjacent 5'-phosphate group is catalyzed by a ligase and a (mis)ligation product is generated.

Amplification according to the present invention encompasses any means by which at least one target nucleic acid sequence, at least a part of at least one (mis)ligation product, at least part of at least one (mis)ligation product surrogate, or combinations thereof, is reproduced, typically in a template-dependent manner, including without limitation, a broad range of techniques for amplifying nucleic acid sequences, either linearly or exponentially (i.e., generating an amplified (mis)ligation product or generating an amplified digested (mis)ligation product). Exemplary means for performing an amplifying step include LCR, PCR, primer extension, strand displacement amplification (SDA), multiple displacement amplification (MDA), nucleic acid strand-based amplification (NASBA), rolling circle amplification (RCA), transcription-mediated amplification (TMA), and the like, including multiplex versions or combinations thereof. Descriptions of such techniques can be found in, among other places, Sambrook and Russell; Sambrook et al.; Ausbel et al.; PCR Primer: A Laboratory Manual, Diffenbach, Ed., Cold Spring Harbor Press (1995); The Electronic Protocol Book, Chang Bioscience (2002)("The Electronic Protocol Book"); Msuih et al., J. Clin. Micro. 34:501-07 (1996); The Nucleic Acid Protocols Handbook, R. Rapley, ed., Humana Press, Totowa, N.J. (2002)(hereinafter "Rapley"); U.S. Pat. No. 6,027,998; PCT Publication Nos. WO 97/31256 and WO 01/92579; Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18- (2002); and Schweitzer and Kingsmore, Curr. Opin. Biotechnol. 12:21-7 (2001).

In certain embodiments, amplification comprises at least one cycle of the sequential procedures of: hybridizing at least one primer with complementary or substantially complementary sequences in at least one target nucleic acid sequence, at least one (mis)ligation product, at least part of at least one (mis)ligation product, at least one (mis)ligation product surrogate, at least part of at least one (mis)ligation product surrogate, or combinations thereof; synthesizing at least one strand of nucleotides in a template-dependent manner using a polymerase; and denaturing the newly-formed nucleic acid duplex to separate the strands. The cycle may or may not be repeated. Amplification can comprise thermocycling or can be performed isothermally. In certain embodiments, newly-formed nucleic acid duplexes are not initially denatured, but are used in their double-stranded form in one or more subsequent steps.

Primer extension is an amplifying technique that comprises elongating at least one probe or at least one primer that is annealed to a template in the 5'=>3' direction using an amplifying means such as a polymerase. According to certain embodiments, with appropriate buffers, salts, pH, temperature, and nucleotide triphosphates, including analogs thereof, i.e., under appropriate conditions, a polymerase incorporates nucleotides complementary to the template strand starting at the 3'-end of an annealed probe or primer, to generate a complementary strand. In certain embodiments, primer extension can be used to fill a gap between two probes of a probe set that are hybridized to target sequences of at least one target nucleic acid sequence so that the two probes can be ligated together. In certain embodiments, the polymerase used for primer extension lacks or substantially lacks 5' exonuclease activity.

The term "quantitative PCR", or "Q-PCR" refers to a variety of well known methods used to quantify the results of the polymerase chain reaction for specific nucleic acid sequences. Such methods typically are categorized as kinetics-based systems, that generally determine or compare the amplification factor, such as determining the threshold cycle ($C_t$), or as co-amplification methods, that generally compare the amount of product generated from simultaneous amplification of target and standard templates. Many Q-PCR techniques comprise reporter probes, intercalating dyes, or both. For example but not limited to TaqMan® probes (Applied Biosystems), i-probes, molecular beacons, Eclipse probes, scorpion primers, LuX™ primers, FRET primers, ethidium bromide, SYBR® Green I (Molecular Probes), and PicoGreen® (Molecular Probes).

Separating comprises any process that removes at least some unreacted components, at least some reagents, or both some unreacted components and some reagents from at least one (mis)ligation product, at least one (mis)ligation product surrogate, or combinations thereof. In certain embodiments, at least one (mis)ligation product or at least part of at least one (mis)ligation product, at least one (mis)ligation product surrogate or at least part of at least one (mis)ligation product surrogate, or combinations thereof, are separated from unreacted components and reagents, including but not limited to, unreacted molecular species present in the sample, ligation reagents, digestion reagents, amplification reagents, for example, but not limited to, unbound/unhybridized ligation probes, primers, enzymes, co-factors, unbound sample components, nucleotides, and the like. The skilled artisan will appreciate that a number of well-known separation means can be useful with the methods disclosed herein.

Exemplary means for performing a separation step include gel electrophoresis, including but not limited to isoelectric focusing and capillary electrophoresis; dielectrophoresis; sorting, including but not limited to fluorescence-activated sorting techniques, such as flow cytometry; chromatography, including but not limited to HPLC, FPLC, size exclusion (gel filtration) chromatography, affinity chromatography, ion exchange chromatography, hydrophobic interaction chromatography, immunoaffinity chromatography, and reverse phase chromatography; affinity tag binding, such as biotin-avidin, biotin-streptavidin, maltose-maltose binding protein (MBP), and calcium-calcium binding peptide; aptamer-target binding; hybridization tag-hybridization tag complement annealing; spectroscopy, including but not limited to MALDI-TOF; and the like. In certain embodiments, at least one (mis)ligation product, at least one (mis)ligation product surrogate, or combinations thereof are bound to one or more substrates and separated from unbound components. Detailed discussion of separation techniques can be found in, among other places, Rapley; Sambrook et al.; Sambrook and Russell; Ausbel et al.; Molecular Probes Handbook; Pierce Applications Handbook; Capillary Electrophoresis: Theory and Practice, P. Grossman and J. Colburn, eds., Academic Press (1992); Wenz and Schroth, PCT International Publication No. WO 01/92579; and M. Ladisch, Bioseparations Engineering: Principles, Practice, and Economics, John Wiley & Sons (2001).

In certain embodiments, at least one separating step comprises at least one mobility-dependent analytical technique, for example but not limited to capillary electrophoresis. In certain embodiments, at least one separating step comprises at least one substrate, for example but not limited to binding at least one biotinylated nucleic acid molecule to at least one streptavidin-coated substrate. Suitable substrates include but are not limited to microarrays, appropriately treated or coated reaction vessels and surfaces, beads, for example but not limited to magnetic beads, latex beads, metallic beads, polymer beads, microbeads, and the like (see, e.g., Tong et al., Nat. Biotech. 19:756-59, 2001; Gerry et al., J. Mol. Biol. 292:251-62, 1999; Srisawat et al., Nucl. Acids Res. 29:e4, 2001; Han et al., Nat. Biotech. 19:631-35, 2001; Stears et al., Nat. Med. 9:140-45, including supplements, 2003). Those in the art will appreciate that the shape and composition of the substrate is generally not limiting. In certain embodiments, a plurality of (mis)ligation products or at least parts (mis)ligation products, (mis)ligation product surrogates or at least parts of (mis)ligation product surrogates, or combinations, thereof are separated via a mobility-dependent analysis technique.

In certain embodiments, at least one (mis)ligation product, at least one (mis)ligation product surrogate, or combinations thereof, are resolved (separated) by liquid chromatography. Exemplary stationary phase chromatography media for use in the teachings herein include reversed-phase media (e.g., C-18 or C-8 solid phases), ion-exchange media (particularly anion-exchange media), and hydrophobic interaction media. In certain embodiments, at least one (mis)ligation product, at least one (mis)ligation product surrogate, or combinations thereof can be separated by micellar electrokinetic capillary chromatography (MECC).

Reversed-phase chromatography is carried out using an isocratic, or more typically, a linear, curved, or stepped solvent gradient, wherein the level of a nonpolar solvent such as acetonitrile or isopropanol in aqueous solvent is increased during a chromatographic run, causing analytes to elute sequentially according to affinity of each analyte for the solid phase. For separating polynucleotides, including (mis)ligation products and at least some (mis)ligation product surrogates, an ion-pairing agent (e.g., a tetra-alkylammonium) may be included in the solvent to mask the charge of phosphate.

The mobility of (mis)ligation products and at least some (mis)ligation product surrogates can be varied by using mobility modifiers comprising polymer chains that alter the affinity of the probe for the solid, or stationary phase. Thus, with reversed phase chromatography, an increased affinity of the (mis)ligation products and at least some (mis)ligation product surrogates for the stationary phase can be attained by adding a moderately hydrophobic tail (e.g., PEO-containing polymers, short polypeptides, and the like) to the mobility modifier. Longer tails impart greater affinity for the solid phase, and thus require higher non-polar solvent concentration for the ligation products and/or ligation product surrogates to be eluted (and a longer elution time).

In certain embodiments, at least one (mis)ligation product, at least one (mis)ligation product surrogate, or combinations thereof, are resolved by electrophoresis in a sieving or non-sieving matrix. In certain embodiments, the electrophoretic separation is carried out in a capillary tube by capillary electrophoresis (see, e.g., Capillary Electrophoresis: Theory and Practice, Grossman and Colburn eds., Academic Press, 1992). Exemplary sieving matrices for use in the disclosed teachings include covalently crosslinked matrices, such as polyacrylamide covalently crosslinked with bis-acrylamide; gel matrices formed with linear polymers (see, e.g., U.S. Pat. No. 5,552,028); and gel-free sieving media (see, e.g., U.S. Pat. No. 5,624,800; Hubert and Slater, Electrophoresis, 16: 2137-2142, 1995; Mayer et al., Analytical Chemistry, 66(10): 1777-1780, 1994). The electrophoresis medium may contain a nucleic acid denaturant, such as 7M formamide, for maintaining polynucleotides in single stranded form. Suitable capillary electrophoresis instrumentation are commercially available, e.g., the ABI PRISM™ Genetic Analyzer series (Applied Biosystems).

In certain embodiments, at least one hybridization tag complement includes at least one hybridization enhancer, where, as used herein, the term "hybridization enhancer" means moieties that serve to enhance, stabilize, or otherwise positively influence hybridization between two polynucleotides, e.g. intercalators (see, e.g., U.S. Pat. No. 4,835,263), minor-groove binders (see, e.g., U.S. Pat. No. 5,801,155), and cross-linking functional groups. The hybridization enhancer may be attached to any portion of a mobility modifier, so long as it is attached to the mobility modifier is such a way as to allow interaction with the hybridization tag-hybridization tag complement duplex. In certain embodiments, at least one hybridization enhancer comprises at least one minor-groove binder, including without limitation, netropsin, distamycin, and the like.

The skilled artisan will appreciate that at least one (mis) ligation product, at least one (mis)ligation product surrogate, or combinations thereof, can also be separated based on molecular weight and length or mobility by, for example, but without limitation, gel filtration, mass spectroscopy, or HPLC, and detected using appropriate methods. In certain embodiments, at least one (mis)ligation product, at least one (mis)ligation product surrogate, or combinations thereof, are separated using at least one of the following forces: gravity, electrical, centrifugal, hydraulic, pneumatic, or magnetism.

In certain embodiments, at least one affinity tag is used to separate the element (e.g., a ligation product, a misligation product, a ligation product surrogate, a misligation product surrogate, etc.) to which it is bound from at least one component of a ligation reaction composition, a digestion reaction composition, an amplified ligation reaction composition, or the like. In certain embodiments, at least one affinity tag is used to bind at least one ligation product, at least one misligation product, at least one ligation product surrogate, at least one misligation product surrogate, or combinations thereof, to at least one substrate, for example but not limited to at least one biotinylated (mis)ligation product to at least one substrate comprising streptavidin. In certain embodiments, at least one aptamer is used to bind at least one ligation product, at least one misligation product, at least one ligation product surrogate, at least one misligation product surrogate, or combinations thereof, to at least one substrate (see, e.g., Srisawat and Engelke, RNA 7:632-641, 2001; Holeman et al., Fold Des. 3:423-31, 1998; Srisawat et al., Nucl. Acid Res. 29(2):e4, 2001).

In certain embodiments, at least one hybridization tag, at least one hybridization tag complement, or at least one hybridization tag and at least one hybridization tag complement, is used to separate the element to which it is bound or annealed from at least one component of a ligation reaction composition, a digestion reaction composition, an amplified ligation reaction composition, or the like. In certain embodiments, hybridization tags are used to attach at least one ligation product, at least one misligation product, at least one misligation product surrogate, at least one ligation product surrogate, or combinations thereof, to at least one substrate. In certain embodiments, at least two (mis)ligation products, at least two (mis)ligation product surrogates, or at least one (mis)ligation product and at least one (mis)ligation product surrogate, comprise the same hybridization tag. In certain embodiments, such a "universal" hybridization tag can then be used for bulk separation, including without limitation, separating a multiplicity of different element:hybridization tag species using the same hybridization tag complement; tethering a multiplicity of different element:hybridization tag species to a substrate comprising the same hybridization tag complement; or both.

In certain embodiments, different ligation products, different misligation products, different ligation product surrogates, different misligation product surrogates, or combinations thereof, are detected by mobility discrimination using separation techniques such as electrophoresis, mass spectroscopy, or chromatography rather than hybridization to capture oligonucleotides on a support. In these embodiments the probes may comprise hybridization tags of unique identifiable lengths or molecular weights. Alternatively, in certain embodiments, a hybridization tag portion of at least one probe is complementary to a particular mobility-modifier comprising a hybridization tag complement for selectively binding to the hybridization tag of the corresponding (mis)ligation product or (mis)ligation product surrogates, and a tail for effecting a particular mobility in a mobility-dependent analytical technique, including without limitation, electrophoresis (see, e.g., U.S. patent application Ser. No. 09/522,640). Thus, the ligation products, misligation products, ligation product surrogates, misligation product surrogates, or combinations thereof, can be separated by molecular weight or length to distinguish the individual sequences. The detection of a (mis) ligation product or a (mis)ligation product surrogate in a particular molecular weight or length bin indicates the presence of the corresponding target sequence in the sample. Descriptions of mobility discrimination techniques may be found, among other places, in U.S. Pat. Nos. 5,470,705; 5,514,543; 5,580,732; 5,624,800; and 5,807,682.

In an exemplary protocol, a variety (mis)ligation products of uniquely identifiable molecular mobility generated from a multiplex OLA or LDR reaction, are diluted in deionized formamide or other suitable diluent. The diluted (mis)ligation products are combined with an electrophoretic size standard (e.g., GS 500 or LIZ 120 size standards, Applied Biosystems) and loaded onto an electrophoresis platform (e.g., ABI Prism™ 3100 Genetic Analyzer, Applied Biosystems) and electrophoresed in POP4 polymer at 15 kV using a 50 µL capillary. The bands are detected and their position relative to the marker is determined and plotted on an electropherogram. The bands are identified based on their relative electrophoretic mobility, indicating the presence of their corresponding target sequence in the sample.

In certain embodiments, at least one ligation product, at least one misligation product, at least one ligation product surrogate, at least one misligation product surrogate, or combinations thereof, comprises at least one hybridization tag containing a sequence that is complementary to a mobility-modifier comprising a hybridization tag complement that corresponds to the hybridization tag portion of at least one ligation product, at least one misligation product, at least one ligation product surrogate, at least one misligation product surrogate, or combinations thereof, and a tail, for effecting a particular mobility in a mobility-dependent analytical technique, such that when the hybridization tag portion and the mobility modifier comprising the corresponding hybridization tag complement are annealed a stable complex is formed (see, e.g., U.S. patent application Ser. No. 09/522,640).

According to certain of these embodiments, hybridization tag portions and hybridization tag complements should form a complex that (1) is stable under conditions typically used in nucleic acid analysis methods, e.g., aqueous, buffered solutions at room temperature; (2) is stable under mild nucleic-acid denaturing conditions; and (3) does not adversely effect a sequence specific binding of a target-specific portion of a probe with a target nucleic acid sequence. In addition, hybridization tag portions and hybridization complements should accommodate sets of distinguishable hybridization tag portions and hybridization tag complements such that a plurality of different (mis)ligation products, (mis)ligation product surrogates, or combinations thereof, and associated mobility modifiers may be present in the same reaction volume without causing cross-interactions among the hybridization tag portions, hybridization tag complements, target nucleic acid sequence and target-specific portions of the probes. Methods for selecting sets of hybridization tag sequences that minimally cross hybridize are described elsewhere (see, e.g., Brenner and Albrecht, PCT Patent Application No. WO 96/41011).

In certain embodiments, at least one hybridization tag and at least one corresponding hybridization tag complement pair includes a hybridization tag comprising conventional synthetic polynucleotide, and a hybridization tag complement that is PNA. PNA and PNA/DNA chimera molecules can be synthesized using well known methods on commercially available, automated synthesizers, with commercially available reagents (see, e.g., Dueholm, et al., J. Org. Chem., 59:5767-73,1994; Vinayak, et al., Nucleosides & Nucleotides, 16:1653-56, 1997).

The hybridization tag portions of certain probes may comprise all, part, or none of the target-specific portion of the probe; likewise, the hybridization tag portions of certain primers may comprise all, part, or none of the complement of the primer-binding portion of corresponding probes. In other embodiments, the hybridization tag portions of certain probes and/or certain primers do not comprise any portion of the target-specific portion of the probe or the complement of the primer-binding portion, respectively.

In certain embodiments, mobility modifiers comprise a hybridization tag complement portion for binding to the corresponding hybridization tag complement of (mis)ligation products, (mis)ligation product surrogates, or combinations thereof, and a tail for effecting a particular mobility in a mobility-dependent analytical technique.

In certain embodiments, the tail portion of a mobility modifier may be any entity capable of affecting a particular mobility of a amplification product/mobility-modifier complex in a mobility-dependent analysis technique. In certain embodiments, the tail portion of the mobility modifier should (1) have a low polydispersity in order to effect a well-defined and easily resolved mobility, e.g., Mw/Mn less than 1.05; (2) be soluble in an aqueous medium; (3) not adversely affect probe-target hybridization or addressable support-specific portion/tag complement binding; and (4) be available in sets such that members of different sets impart distinguishable mobilities to their associated complexes.

In certain embodiments of the teachings herein, the tail portion of the mobility modifier comprises a polymer. Specifically, the polymer forming the tail may be homopolymer, random copolymer, or block copolymer. Furthermore, the polymer may have a linear, comb, branched, or dendritic architecture. In addition, although the invention is described herein with respect to a single polymer chain attached to an associated mobility modifier at a single point, the invention also contemplates mobility modifiers comprising more than one polymer chain element, where the elements collectively form a tail portion.

Certain polymers for use herein are hydrophilic, or at least sufficiently hydrophilic when bound to a hybridization tag complement to ensure that the hybridization tag complement is readily soluble in aqueous medium. Where the mobility-dependent analytical technique is electrophoresis, the polymers are preferably uncharged or have a charge/subunit density that is substantially less than that of the (mis)ligation product or (mis)ligation product surrogate.

In certain embodiments, the polymer is polyethylene oxide (PEO), e.g., formed from one or more hexaethylene oxide (HEO) units, where the HEO units are joined end-to-end to form an unbroken chain of ethylene oxide subunits. Other exemplary embodiments include a chain composed of N 12mer PEO units, and a chain composed of N tetrapeptide units, where N is an adjustable integer (see, e.g., U.S. Pat. No. 5,777,096).

The synthesis of polymers useful as tail portions of a mobility modifier of the current teachings will depend on the nature of the polymer. Methods for preparing suitable polymers generally follow well known polymer subunit synthesis methods. Methods of forming selected-length PEO chains are discussed below. These methods, which involve coupling of defined-size, multi-subunit polymer units to one another, either directly or through charged or uncharged linking groups, are generally applicable to a wide variety of polymers, such as polyethylene oxide, polyglycolic acid, polylactic acid, polyurethane polymers, polypeptides, and oligosaccharides. Such methods of polymer unit coupling are also suitable for synthesizing selected-length copolymers, e.g., copolymers of polyethylene oxide units alternating with polypropylene units. Polypeptides of selected lengths and amino acid composition, either homopolymer or mixed polymer, can be synthesized by standard solid-phase methods (e.g., Fields and Noble, Int. J. Peptide Protein Res., 35: 161-214, 1990).

According to one method for preparing PEO polymer chains having a selected number of HEO units, an HEO unit is protected at one end with dimethoxytrityl (DMT), and activated at its other end with methane sulfonate. The activated HEO is then reacted with a second DMT-protected HEO group to form a DMT-protected HEO dimer. This unit-addition is then carried out successively until a desired PEO chain length is achieved (e.g., U.S. Pat. No. 4,914,210).

PNA is another polymer that can be used as a tail portion according to the current teachings. The advantages, properties and synthesis of PNA have been described above. In particular, when used in the context of a mobility-dependent analytical technique comprising an electrophoretic separation in free solution, PNA has the advantageous property of being essentially uncharged.

Coupling of the polymer tails to a hybridization tag complement can be carried out by an extension of conventional phosphoramidite polynucleotide synthesis methods, or by other standard coupling methods, e.g., a bis-urethane tolyl-linked polymer chain may be linked to an polynucleotide on a solid support via a phosphoramidite coupling. Alternatively, the polymer chain can be built up on a polynucleotide (or other tag portion) by stepwise addition of polymer-chain units to the polynucleotide, e.g., using standard solid-phase polymer synthesis methods.

As noted above, the tail portion of the mobility modifier imparts a mobility to a (mis)ligation product (surrogate): mobility modifier complex that is distinctive for each different complex. The contribution of the tail to the mobility of the complex will in generally depend on the size of the tail. However, addition of charged groups to the tail, e.g., charged linking groups in the PEO chain, or charged amino acids in a polypeptide chain, can also be used to achieve selected mobility characteristics in the probe/mobility modifier complex. Those in the art will also understand that the mobility of a complex may be influenced by the properties of the (mis)ligation product or (mis)ligation product surrogate, e.g., in electrophoresis using a sieving medium, a larger probe will reduce the electrophoretic mobility of the probe/mobility modifier complex.

In certain embodiments, the hybridization tag complement portion of a mobility modifier may be any entity capable of binding to, and forming a complex with, the corresponding hybridization tag of a ligation product, misligation product, ligation product surrogate, misligation product surrogate, or combinations thereof. Furthermore, the hybridization tag complement portion of the mobility modifier may be attached to the tail portion using conventional means.

When a hybridization tag complement is a polynucleotide, e.g., PNA, the hybridization tag complement may comprise all, part, or none of the tail portion of the mobility modifier. In some embodiments, the hybridization tag complement may consist of some or all of the tail portion of the mobility modifier. In other embodiments, the hybridization tag complement does not comprise any portion of the tail portion of the mobility modifier. For example without limitation, because PNA is uncharged, particularly when using free solution electrophoresis as the mobility-dependent analysis technique, the same PNA oligomer may act as both a hybridization tag complement and a tail portion of a mobility modifier.

According to certain embodiments, a plurality of (mis) ligation product (surrogate)/mobility modifier complexes are resolved via a mobility-dependent analytical technique.

Identifying at least one target nucleotide in a mixed population comprises detecting at least one reporter group that corresponds to at least one ligation product, at least one misligation product, at least one ligation product surrogate, at least one misligation product surrogate, or combinations thereof. According to the present teachings, identifying comprises determining the presence or absence of a particular ligation product, a particular ligation product surrogate, or combinations thereof, particularly when hybridized to a support or occupying a particular mobility address during a mobility dependent analytical technique. For example, when the hybridization tag of a ligation product, ligation product surrogate, or their complement, specifically hybridizes to the hybridization tag complement on a substrate, the hybridized sequence can be detected provided that a reporter group is present. Typically, the reporter group provides an emission that is detectable or otherwise identifiable in the detection step. The type of detection process used will depend on the nature of the reporter group to be detected. For example without limitation, a particular detection step used in combination with a fluorescent reporter group, the fluorescent reporter group is detected using laser-excited fluorescent detection.

In certain embodiments, identifying further comprises quantifying at least one detected ligation product, at least one detected ligation product surrogate, or combinations thereof, for example but not limited to graphically displaying the quantified at least one ligation product, at least one ligation product surrogate, or combinations thereof, on a graph, monitor, electronic screen, magnetic media, scanner print-out, or other two- or three-dimensional display. Typically the peak height, the area under the peak, the signal intensity of one or more detected reporter group on at least one ligation product, at least one ligation product surrogate, or combinations thereof, or other quantifiable parameter of the ligation product or ligation product surrogate are measured and the quantity of ligation product that was generated in a particular ligation assay can be extrapolated using, for example but without limitation, one or more corresponding standard curves, from which the quantity of the target nucleotide that corresponds to that ligation product can be inferred. In certain embodiments, at least one quantified parameter for at least one ligation product, at least one ligation product surrogate, or combinations thereof, generated by one ligase for one target nucleotide is compared to the same parameter(s) for a ligation product, ligation product surrogate, or combinations thereof, generated by a ligase for a corresponding second nucleotide (including but not limited to the wild-type and mutant nucleotide for related viruses, cell types, or the like) and the ligation rate or ratio of the two ligation products is obtained to identify the percentage of the two target nucleotides present in the sample.

In certain embodiments, at least one identifying step comprises detecting and quantifying at least one ligation product parameter using at least one instrument, i.e., using an automated or semi-automated determining means that can, but need not, comprise a computer algorithm. In certain embodiments, the identifying step is combined with or is a continuation of at least one separating step, for example but not limited to a capillary electrophoresis instrument comprising at least one fluorescent scanner and at least one graphing, recording, or readout component; a chromatography column coupled with an absorbance monitor or fluorescence scanner and a graph recorder; or a microarray with a data recording device such as a CCD camera. Exemplary means for performing a separating step include the ABI PRISM® 3100 Genetic Analyzer, ABI PRISM® 3100-Avant Genetic Analyzer, ABI PRISM® 3700 DNA Analyzer, ABI PRISM® 3730 DNA Analyzer, ABI PRISM(® 3730x/DNA Analyzer (all from Applied Biosystems); the ABI PRISM® 7300 Real-Time PCR System; and microarrays and related software such as the ABI PRISM® 1700 (Applied Biosystems) and other commercially available array systems available from Affymetrix, Agilent, and Amersham Biosciences, among others (see also Gerry et al., J. Mol. Biol. 292:251-62, 1999); De Bellis et al., Minerva Biotec 14:247-52, 2002; and Stears et al., Nat. Med. 9:140-45, including supplements, 2003). Exemplary software includes GeneMapper™ Software, GeneScan® Analysis Software, and Genotyper® software (all from Applied Biosystems).

The generation of misligation products may be undesirable in certain ligation-based assays, depending on their application, while for other applications, the generation of misligation products may be desired. For example, conventional SNP genotyping typically is used to evaluate whether a given individual is homozygous or heterozygous at a particular SNP site. For illustration purposes, assume that SNP site 1 has two possible alleles T and G. Thus one expects the assay to identify the SNP as all T or all G if the individual is homozygous, or approximately half T and half G if the individual is heterozygous for SNP 1. Consequently, if the ligation assay results indicate, for example, 85% G (the match ligation product) and 15% T, due to mismatch ligation, the individual would likely be identified as a G homozygote at SNP 1. However, for certain ligation-based assay applications, such as analyzing nucleic acid sequences that from more than one individual, the presence of detectable misligation products could result in an incorrect determination.

According to the present teachings, the disclosed methods and kits can be used to identify the emergence and prevalence of drug-resistant mutant viruses in patients undergoing antibiotic, antiviral, and/or chemotherapy regimens. By way of illustration, but without limitation, the drug-resistant mutant viruses in an AIDS patient undergoing antiviral therapy, such as protease and/or reverse transcriptase inhibitor drugs, can be evaluated using the disclosed methods and kits. For example, AIDS patients receiving protease inhibitors frequently develop a mutation, D30N, in the viral protease (see, e.g., Shafer et al., J. Virol. 73(7):6197-202, 1999; Patrick et al., Antimicrob. Agents Chemother. 42:2637-44, 1998). If cDNA is generated from the viral nucleic acid in the blood sample of a patient that contains some viruses with the "wild-type" aspartic acid codon (GAT) and also mutant viruses with the "mutant" asparagine codon (AAT), at least one probe set can be designed to identify the presence of and quantity of each of the exemplary target nucleotides, G or A. Thus, an exemplary probe set would comprise at least one first upstream probe would comprise a "C" nucleotide at its 3'-end and a first reporter group, at least one second upstream probe would comprise a "T" nucleotide at its 3'-end and a second reporter group, and a common downstream probe. To minimize the generation of misligation products, a first ligation reaction composition would comprise viral cDNA target nucleic acid sequences, at least one first upstream probe, at least one downstream probe, and AK16D ligase; and a second ligation reaction composition would comprise viral cDNA target nucleic acid sequences, at least one second upstream probe, at least one downstream probe, and Afu ligase. The two ligation reaction compositions are subjected to a multiplicity of ligation cycles in parallel to generate first and second ligation products, respectively. The first and second ligation products are identified using an ABI PRISM® 3100 Genetic Analyzer and the percentage of the first and second target nucleotides present in the patients blood is quantified using corresponding standard curves.

Those in the art understand that this process can be multiplexed to, for example but not limited to, monitor the appearance and prevalence of a multiplicity of drug resistant mutants. For example, one can obtain the sequence for numerous drug resistant mutants in the scientific/medical literature and electronic/internet databases or one can experimentally determine one or more mutation sites. Appropriate probe sets can be synthesized and, when matched with appropriate ligases (e.g., chosen to eliminate or at least decrease misligation products), can be used to monitor for example but not limited to the temporal emergence or variants for epidemiological purposes, changing drug susceptibilities of the viruses within a patient to allow appropriate treatment regimes, and so forth. Likewise, bacterial drug resistant mutants and cellular resistance to chemotherapeutics can be monitored in a similar manner, allowing physicians to change the patient's antibiotic or chemotherapy regimens as necessary.

Similarly, the current teachings can be employed to identify virtually any point mutation, deletion, or insertion using appropriate probe sets and ligases to at least minimize misligation products. Further, chromosomal translocations can also be identified using the ligation-based assays disclosed herein, for example but without limitation, a pair of upstream probes can be synthesized, one that hybridizes to the "normal" nucleic acid sequences upstream of the predicted translocation site and the other that hybridizes to the translocated sequences immediately upstream of the predicted translocation site, with a common downstream probe that hybridizes to the "normal" sequences immediately downstream of the translocation site that are present whether a translocation event has occurred or not. When adjacently hybridized and in the presence of an appropriate ligase, the upstream and downstream probes can be ligated to generate a ligation product. When that ligation product is detected, one can identify whether and to what extent, a chromosomal translocation event has occurred, provided that the ligation products are quantified and evaluated, using for example but not limited to, one or more standard curve.

Standard curves can be useful for quantifying the amount of a particular target nucleotide in a sample, including without limitation, the percentage of a particular drug resistant virus emerging in a patient or the percentage of malignant cells in a tissue biopsy sample. Standard curves can be generated, for example but not limited to, using pre-determined mixtures of synthetic templates or gDNA comprising the target nucleotide(s) of interest as the target nucleic acid sequences in one or more of the disclosed ligation assays under standard conditions. By comparing one or more experimentally-determined ligation product parameter obtained from an unknown sample with standard curves for the same target nucleotide and using the same probes and assay conditions, one can quantify the amount of the target nucleotide in the sample by extrapolating values from the standard curve.

The generation and use of standard curves is well known to those in the art (see, e.g., Overholtzer et al., Proc. Natl. Acad. Sci. 100:11547-52, 2003). Typically, a standard curve is generated by plotting experimentally obtained results for a particular set of reagents and under defined assay conditions on an X-Y graph or other coordinate system and then generating a curve, generally either manually or using one or more mathematical formula or algorithm, for example but not limited to graphing and/or line drawing software, linear regression analysis and similar mathematical calculations, computer algorithms, or the like. Once a standard curve have been generated for a given target nucleotide and at least one corresponding probe set or at least an appropriate subset of at least one corresponding probe set, experimentally-determined results obtained from test (unknown) samples using the same probes under the same assay conditions can be evaluated using the standard curve and the quantity or percentage of a target nucleotide in a sample can be extrapolated. The skilled artisan will appreciate that a "curve" can actually be a straight or substantially straight line or it can be curvilinear and assume a wide range of shapes.

For illustration purposes, but without limitation, to generate a standard curve for quantifying the amount of a particular target nucleotide in a sample, ligation assays are performed under set ("standard") conditions using appropriate probes, but with at least two target compositions comprising different known amounts of target nucleotide sequences with and without the particular target nucleotide, for example without limitation, a specific transforming mutation in a proto-oncogene in a biopsy specimen. An illustrative three sample assay where a first ligation reaction composition includes only target nucleic acid sequences comprising the wild-type sequence (0% mutant target nucleotide), a second ligation reaction composition comprises a 1:1 mixture of wild-type and mutant target nucleotide sequences (50% mutant target nucleotide), and the third ligation reaction composition comprises target nucleic acid sequences that all contain the mutant target nucleotide (100% mutant target nucleotide) and a three point standard curve, using the ligation product ratios corresponding to 0, 50 and 100% mutant target nucleotide, is generated; a four sample assay where a first ligation reaction composition comprises all wild-type target nucleic acid sequences (0% mutant target nucleotide), a second ligation reaction composition comprises a 1:2 mixture of mutant: wild-type target nucleotide sequences (33.3% mutant target nucleotide), a third product reaction composition comprises a 2:1 mixture of mutant:wild-type target nucleotide sequences (66.6% mutant target nucleotides) and the fourth ligation reaction composition includes only mutant target nucleic acid sequences (100% mutant target nucleotides) a four point standard curve, based on the ligation product ratios corresponding to 33.3, 50 and 100% mutant target nucleotides, is generated; and so forth. The skilled artisan appreciates that the accuracy of standard curves generally increases as the number of data points used to generate the curve increases and also as the number of replicate assays are performed. Those in the art also appreciate that controls and/or calibration standards can be included either with unknowns or run in parallel.

According to the present teachings, at least one step for interrogating at least one target nucleotide is performed using the disclosed probes and probe sets; at least one step for generating at least one ligation product is performed using the disclosed ligation agents and ligation techniques; at least one step for generating at least one amplified ligation product and/or ligation product surrogate is performed using the disclosed amplifying means and amplification techniques; at least one step for generating at least one digested ligation product is performed using the disclosed nucleases, restriction enzymes, chemical digesting means, and digestion techniques; and at least one step for identifying at least one target nucleotide is performed using at least one disclosed detecting technique, at least one quantifying technique, at least one evaluating technique, at least one disclosed separating technique, or combinations thereof.

III. Exemplary Embodiments

The current teachings, having been described above, may be better understood by reference to examples. The following examples are intended for illustration purposes only, and should not be construed as limiting the scope of the teachings herein in any way.

The present teachings are directed to methods, reagents, and kits that are useful for generating at least one ligation product and/or identifying at least two target nucleotide in a mixed or potentially mixed population sample. The skilled artisan will appreciate that when analyzing genomic DNA there are typically multiple copies of target nucleic acid sequences in the sample being evaluated, at least some of which contain the target nucleotides. The identity of, including the quantity or percentage of, a particular target nucleotide is generally determined from the sum of at least some of the ligation products obtained using at least part of that population of target nucleic acid sequences.

In certain embodiments, at least one target nucleotide is identified by comparing one or more quantified parameters between two or more ligation products or their surrogates, at least one quantified ligation product parameter and one or more standard curve, or both. In certain embodiments, at least one probe set comprises one or more nucleotides on or near the 3'-end of the upstream probe, on or near the 5'-end of the downstream probe, or both, that are not complementary to the corresponding nucleotide(s) on the target nucleic acid sequence. The corresponding nucleotide on the target nucleic acid sequence can, but need not, be the target nucleotide. In certain embodiments, the ligation site comprises the nucleotide opposing the target nucleotide. Those in the art will appreciate that the terms upstream or 5' probe and downstream or 3' probe are used in reference to their annealing position on the corresponding target nucleic acid sequence in the 3'=>5' orientation.

EXAMPLE 1

Cloning and Expression of Afu Ligase

*Archaeoglobus fulgidus* gDNA was purchased from ATCC (catalog #49558D). Two oligonucleotides derived from the seq uence of the putative Afu ligase gene (Gen Bank seq. AF0623) were designed: a 5'-primer containing an NdeI site (in bold), 5'-CATATGATGTTGTTTGCCGAGTTTG-3' (SEQ ID NO: 90), and a 3' primer containing a Sal I site (in bold), 5'-TCGACTCATTGTCTCTTTACCTCGAACTG-3' (SEQ ID NO: 91). The polymerase chain reaction (POR) was performed under the following conditions: 1×Pfu buffer (Stratagene), 200 mM each dNTP (Pharmacia), 5 pmol each primer, 70 ng gDNA and 2.5 u of Pfu HotStart DNA polymerase (Stratagene) were combined in reaction composition with a final volume of 25 µL. Cycling conditions were: 95° C. for 2 minutes followed by 30 cycles (96° C. for 5s, 60° C. for 30s, 7200 for 2 minutes) followed by 70° C. for 10 minutes. The POR amplified fragment was gel-purified. To enable the use of the TOPO cloning vector (Invitrogen) the PCR fragment was incubated with Taq DNA polymerase for the non-templated addition of adenine. The resulting fragment was cloned into PCR 4 TOPO TA vector (Invitrogen) according to the manufacturer's protocol. The presence of the putative ligase gene was confirmed by DNA sequencing and the resulting plasmid was subcloned into the pET24a expression vector. *E. coil* CodonPlus BL21 (DE3) (Stratagene) was used for protein expression. Overnight cultures were grown in LB medium containing 50 µg/mL chloramphenicol and 50 µg/mL kanamycin. The next morning 1.5 L of LB medium without antibiotics was inoculated with 75 ml of the overnight culture and incubated at 37° C. with shaking at 250 rpm for 2 hours. Protein synthesis was induced by the addition of iso-propyl-D-thiogalactopyranoside (IPTG) to a final concentration of 1 mM. After 2 hours of induction, cells were harvested (5,000×g, 20 mm, 4° C.) and the cell pellets were stored at −80° C.

EXAMPLE 2 rAfu Ligase Purification

The cell pellets from Example 1 were re-suspended in buffer A at $\frac{1}{10}^{th}$ of the original volume (buffer A: 50 mM Tris-HCl [pH 7.5]). The cells were disrupted by sonication and the lysate clarified by centrifugation (12,000×g, 20 min, 4° C.). The soluble fraction of the lysate was pasteurized at 85° C. for 25 min followed by 10 minutes on ice. Precipitated *E. coli* proteins were removed by centrifugation (12,000×g, 20 min, 4° C.). An anion exchange column (Macro-Prep High Q, Bio-Rad, Hercules, Calif.) and a cation exchange column (Macro-Prep High S, Bio-Rad, Hercules, Calif.) were connected in series and both equilibrated with buffer A. The supernatant was applied first to the anion-exchange resin and the flow-through applied directly to the cation-exchange column. The recombinant Afu ligase (rAfu) did not bind to the anion exchange resin. The cation exchange column was washed with buffer A until the background returned to zero. The enzyme was eluted with a 0 to 1.0 M $MgCl_2$ linear gradient with buffer A. The rAfu eluted between 0.15 and 0.30 M $MgCl_2$. Peak fractions were analyzed by SDS-PAGE gel electrophoresis. Fractions containing rAfu were pooled, concentrated and desalted with an Amicon pressure concentrator cell (Millipore, Bedford, Mass.) and mixed 1:1 with storage buffer (90% glycerol in a buffer containing 20 mM Tris, pH 8.5, 0.1 mM EDTA, 0.05% Triton X-100, 0.05% Tween 20). Resulting purified rAfu ligase was stored at −20° C. The protein concentration was determined by the Bio-Rad protein assay system (Bio-Rad, Hercules, Calif.) using bovine serum albumin as a standard. DNA ligation activity was measured with the thermostable units assay as described for Taq DNA ligase (New England Biolabs, Beverly, Mass.), with 1 unit defined as the amount of enzyme that ligates 50% of bacteriophage λ cos-sites of 1 µg Hind III λ-DNA in 15 min at 45° C.

EXAMPLE 3

Oligonucleotide Synthesis

The synthetic oligonucleotides described herein, including templates, probes, and primers, were prepared as follows. Oligonucleotides were synthesized on an ABI PRISM® 380A DNA Synthesizer using N,N-diisopropylphosphoramidites, controlled-pore glass columns, and synthesis reagents (all from Applied Biosystems, Foster City, Calif.) using a 10-fold excess of protected phosphoramidites and 1 µmole of nucleotide bound to the synthesis support column according to the manufacturer's protocols. The 5'-end of all of the downstream (3'-) probes in the examples described herein were chemically phosphorylated to render them suitable for ligation. The synthesis was performed according to the manufacturer's instructions (see also, Matteucci, et al., Journal Amer. Chem. Soc., 103:3185-3319, 1981; McBride, et al., Tetrahedron Letters, 24:245-248, 1983). The repetitive yield of the synthesis, as measured by the optical density of the removed protecting group, was greater than 97.5%. The crude oligonucleotide mixtures were purified by preparative HPLC.

EXAMPLE 4

Ligase Fidelity Using Synthetic Templates

To assess the fidelity of Afu ligase relative to that of two *Thermus* species ligases, a series of synthetic templates (derived from the −21 primer of bacteriophage M13) and a corresponding ligation probe set were generated on an ABI PRISM® 380A DNA Synthesizer, as described in Example 3. The four M13-derived templates, each differing by a single nucleotide at the ligation site (underlined), are shown in Table 1.

TABLE 1

M13-Derived Templates

| Template No. | Sequence and SEQ ID NO: |
|---|---|
| 1 | ACATTTTGCTGCCGGTCACGGTTCGAACGTACGGACG (SEQ ID NO.: 1) |
| 2 | ACATTTTGCTGCCGGTCTCGGTTCGAACGTACGGACG (SEQ ID NO.: 2) |
| 3 | ACATTTTGCTGCCGGTCGCGGTTCGAACGTACGGACG (SEQ ID NO.: 3) |
| 4 | ACATTTTGCTGCCGGTCCCGGTTCGAACGTACGGACG (SEQ ID NO.: 4) |

The probe set, derived from the −21M13 primer, comprised a single downstream probe and four upstream probes, as shown in Table 2. The single downstream probe, an LSO in this example, comprised the fluorescent reporter group FAM® (Fam). The four upstream probes each comprised the same template-specific sequence except for the 3′ nucleotide and three of the four further comprised additional T residues that served as mobility modifiers (shown in brackets).

TABLE 2

Probe Set derived from the −21 primer of bacteriophage M13 (−21M13).

| Upstream Probes | Downstream Probe |
|---|---|
| TGTAAAACGACGGCCAGT (SEQ ID NO: 5; probe no. 5) | pGCCAAGCTTCGATGC CTG C-Fam (SEQ ID NO: 6) |
| [TTTT] TGTAAAACGACGGCCAGA (SEQ ID NO: 7; probe no. 7) | |
| [TTTTTTTT] TGTAAAACGACGGCCAGC (SEQ ID NO: 8; probe no. 8) | |
| [TTTTTTTTTTTT] TGTAAAACGACGGCCAGG (SEQ ID NO: 9; probe no. 9) | |

Individual ligation reaction compositions comprising: a ligase (either Taq ligase, AK1 6D ligase, or Afu ligase); one of the four templates shown in Table 1; and the ligation probe set shown in Table 2; were prepared as follows. A series of 10× DNA premixes for each template and corresponding ligation probe set were prepared comprising 400 nM of the common downstream probe, 200 nM of each of the four upstream probes, and 800 nM of one of the synthetic templates in appropriate ligation buffer (50 mM Tris-HCl pH 7.5, 10 mM MgCl$_2$, 10 mM DTT, 1 mM ATP, and 0.1% Triton X-100 for Afu ligase; 20 mM Tris-HCl pH 7.6, 25 mM KAc, 10 mM MgCl$_2$, 10 mM DTT, 1 mM NAD and 0.1% Triton X-100 for either of the *Thermus* ligases). Each DNA premix was heated to 90° C. then slowly cooled to 40° C. over ten minutes in the block of a Model 9600 Thermocycler (Perkin Elmer) using the ramp function, allowing hybridization complexes to form. Five μL of each premix comprising double-stranded hybridization complexes was combined with 45 μL of the ligase/buffer mixture (Taq ligase (New England BioLabs), AK16D ligase (prepared as described in Tong et al., Nucl. Acids Res. 27(3):788-94, 1999) or Afu ligase, each in appropriate ligation buffer). These ligation reaction compositions were placed in the thermocycler at 45° C.

Each reaction was stopped by combining a 5 μL aliquot of the cycled ligation reaction composition with 10 μL 100 mM EDTA and chilled on ice. For the matched ligation reactions, aliquots were obtained after 2 minutes (min.), 5 min., 10 min., 20 min., 30 min., and 60 min. reaction time; for the mismatched ligation reactions, aliquots were obtained after 10 min., 20 min., 30 min., 60 min., 4 hours (hr.), 10 hr., 21 hr. and 22 hr. reaction time. Each of these stopped reaction compositions was diluted 40-fold in distilled deionized water and a 5 μL aliquot of the diluted ligation products was combined with 20 μL HiDi™ formamide containing 0.2 μL LIZ™ 120 size standards. These diluted ligation products were separated by electrophoresis using 36 cm capillaries with POP4 polymer on an ABI PRISM® 3100 Genetic Analyzer and the resulting electropherograms were analyzed using GeneScan version 2.1 software (all from Applied Biosystems). Relative yield was calculated as the ratio of the peak area of the ligation product compared to the total peak areas of the ligation product and unreacted ligation probes. Under steady state conditions, i.e., relative yield <20%, ligation product formation was linear with time. Only data in the linear range was considered in this and other examples described herein, except for data from the zero time point. The mismatch ligation rates, normalized to the rate of matched ligation using the same upstream probe, are shown in Table 3.

TABLE 3

Relative rates of mismatch ligation for Taq ligase, AK16D ligase, and Afu ligase using M-13 derived probes and templates.

| probe no. (3′ nucleotide) | Template (target nucleotide) | Taq ligase | AK16D ligase | Afu ligase |
|---|---|---|---|---|
| 9 (G) | 1 (A) | — | — | — |
| 9 (G) | 2 (T) | 0.03% | 0.04% | — |
| 9 (G) | 3 (G) | — | — | — |
| 5 (T) | 4 (C) | 0.07% | 0.04% | 1.51% |
| 5 (T) | 2 (T) | 0.01% | 0.03% | — |
| 5 (T) | 3 (G) | 0.25% | 0.22% | — |
| 7 (A) | 4 (C) | 0.05% | 0.05% | 1.68% |
| 7 (A) | 1 (A) | — | — | — |
| 7 (A) | 3 (G) | — | — | — |
| 8 (C) | 4 (C) | — | — | — |
| 8 (C) | 1 (A) | 0.04% | 0.06% | 0.92% |
| 8 (C) | 2 (T) | — | — | 0.33% |

"—" indicates no detectable misligation in all tables.

Comparing the experimentally determined mismatch ligation rates for Afu and Taq ligases, we find that: (a) for 3′T:C mismatches, the ratio is greater than 21 (1.51/0.07), (b) for 3′A:C mismatches, the ratio is greater than 33 (1.68/0.05), and (c) for 3′C:A mismatches, the ratio is 23 (0.92/0.04). Thus, under these reaction conditions and using these templates and probes, Afu ligase efficiently misligates 3′T:C, 3' A:C, 3'C:A, and 3'C:T mismatches compared to either of the *Thermus* species ligases. Conversely, each of the *Thermus* species ligases by definition efficiently misligate the 3'T:G mismatch compared to Afu ligase (i.e., 0.25 or 0.22 compared to no detectable misligation product).

EXAMPLE 5

Ligase Fidelity Analysis Using Y-Chromosome SNPs

To further evaluate the fidelity of Afu ligase relative to three *Thermus* species ligases (Taq ligase, AK16D ligase and *T. scotoductus* (Tsc) ligase (Roche)) a set of five of human Y-chromosome SNP sites were selected and corresponding ligation probe sets synthesized. The synthetic Y-chromosome template sequences are shown in Table 4 (SNP sites shown underlined).

TABLE 4

Synthetic Y-chromosome Templates (in 3' => 5' orientation).

| Y-SNP | Template sequence |
|---|---|
| YT37C1 | GCGACACTGCGCACGATTTCATGGAAACAACA (SEQ ID NO: 10) |
| YT37G2 | GCGACACTGCGCAGGATTTCATGGAAACAACA (SEQ ID NO: 11) |
| YT40A1 | AGTTTATAGGTCAAATATCTACAGCAAACTCTTCACCGCC (SEQ ID NO: 12) |
| YT40T2 | AGTTTATAGGTCAAATATCTACTGCAAACTCTTCACCGCC (SEQ ID NO: 13) |
| YT46C1 | TCAGCACAAAAGCCTAACAGAGAAAAACTTCAAACCTAA (SEQ ID NO: 14) |
| YT46T2 | TCAGCACAAAAGCCTAATAGAGAAAAACTTCAAACCTAA (SEQ ID NO: 15) |
| YT67RA1 | GCACTGTTGTAAAGCCTGAGTATTTTACTTGGCAGCT (SEQ ID NO: 16) |
| YT67RC2 | GCACTGTTGTAAAGCCTGCGTATTTTACTTGGCAGCT (SEQ ID NO: 17) |
| YT84A1 | CAGGCAAAGTGAGAGATAAGATTTTTGTACATAACCTTAG (SEQ ID NO: 18) |
| YT84G2 | CAGGCAAAGTGAGAGATGAGATTTTTGTACATAACCTTAG (SEQ ID NO: 19) |

Each probe set comprised two upstream probes (referred to as ASO1 and ASO2 in this example), each being complementary with one of the two SNP alleles and one downstream probe (referred to as LSO in this example). As shown in Table 5, the two ASOs in a given probe set each had a different nucleotide on its 3'-end (underlined) to allow complementarity with its corresponding allele and the two probes; additionally, the probes in each probe set differed from each other based on mobility modifiers (shown in brackets). The LSO in each ligation probe set comprised a fluorescent reporter group (DR110, DTAMRA, dR6G; see U.S. Pat. No. 6,025,505).

TABLE 5

OLA Probes for Y-Chromosome SNP analysis.

| dsSNP SNP dbase* | ASO1 | ASO2 | LSO |
|---|---|---|---|
| Y37 rs2032653 | TGTTGTTTCCATGAAATCC (SEQ ID NO: 20; probe 20) | $[T]_{12}$GTTTCATGAAATCG (SEQ ID NO: 21; probe 21) | pTGCGCAGTGTCGC-DR110 (SEQ ID NO: 22) |
| Y40 rs2072422 | $[T]_{22}$GCGGTGAAGAGTTTGCA (SEQ ID NO: 23; probe 23) | $[T]_{10}$GCGGTGAAGAGTTTGCT (SEQ ID NO: 24; probe 24) | pGTAGATATTTGACCTATAAACT-DTAMRA (SEQ ID NO: 25) |
| Y46 rs2196155 | $[T]_5$TTAGGTTTGAAGTTTTTCTCTA (SEQ ID NO: 26; probe 26) | $[T]_{17}$TTAGGTTTGAAGTTTTTCTCTG (SEQ ID NO: 27; probe 27) | pTTAGGCTTTTGTGCTGA-DR110 (SEQ ID NO: 28) |
| Y67 rs1558843 | AGCTGCCAAGTAAAATACT (SEQ ID NO: 29; probe 29) | $[T]_{12}$CAAGTAAAATACG (SEQ ID NO: 30; probe 30) | pCAGGCTTTACAACAGTGC-dR6G (SEQ ID NO: 31) |
| Y84 rs2032652 | CTAAGGTTATGTACAAAAATCTC (SEQ ID NO: 32; probe 32) | $[T]_{11}$CTAAGGTTATGTACAAAAATCTT (SEQ ID NO: 33; probe 33) | pATCTCTCACTTTGCCTG-DTAMRA (SEQ ID NO: 34) |

*the dsSNP database is found on the world wide web at ncbi.nlm.nih.gov/SNP/index Ligation reaction compositions and reactions were performed as described in Example 4, except that the templates and corresponding probes shown in Tables 4 and 5 were used. As shown in Table 6, Afu ligase displays lower fidelity in this ligation assay under these conditions than any of the *Thermus* species ligases with respect to 3'C:C and 3'T:C mismatch ligations. In contrast, the *Thermus* species ligases generally display lower fidelity in this assay under these conditions than Afu ligase with respect to 3'G:T and 3'T:G mismatch ligations.

TABLE 6

Relative rates of mismatch ligation for the Y-Chromosome Panel (normalized to the rate of matched ligation using the corresponding matched ASO).

| Y-SNP (SNP nt) | Probe No. (3'nt) | Mismatch | Taq ligase | AK16D ligase | Tsc ligase | Afu ligase |
|---|---|---|---|---|---|---|
| YT37(C) | 20 (C) | 3'C:C | — | — | — | 0.16% |
| YT37(G) | 21 (G) | 3'G:G | — | — | — | — |
| YT40(A) | 23 (A) | 3'A:A | — | — | — | — |
| YT40(T) | 24 (T) | 3'T:T | — | — | — | — |
| YT46(C) | 26 (A) | 3'A:C | — | — | 0.08% | — |
| YT46(T) | 27 (G) | 3'G:T | 4.21% | 0.32% | 0.13% | — |
| YT67(A) | 30 (G) | 3'G:A | — | — | — | — |
| YT67(C) | 29 (T) | 3'T:C | — | — | — | 0.33% |

TABLE 6-continued

Relative rates of mismatch ligation for the Y-Chromosome Panel (normalized to the rate of matched ligation using the corresponding matched ASO).

| Y-SNP (SNP nt) | Probe No. (3'nt) | Mismatch | Taq ligase | AK16D ligase | Tsc ligase | Afu ligase |
|---|---|---|---|---|---|---|
| YT84(A) | 33 (C) | 3'C:A | 2.85% | — | — | — |
| YT84(G) | 34 (T) | 3'T:G | 1.80% | 1.26% | — | — |

EXAMPLE 7

Ligation Fidelity Analysis Using gDNA in a Multiplexed PCR-OLA

To evaluate the fidelity of Afu ligase relative to Taq ligase using gDNA templates, ligation probe sets corresponding to nine Y-chromosome SNPs were synthesized as described in Example 3. Four gDNA samples were obtained from the Coriell Cell Repository, Camden, N.J. (sample #35: NA 15506; sample #41: NA15283; sample #45: NA15025; and sample #158: NA 15323). The nine Y-chromosome SNPs and corresponding ligation probe sets are shown in Tables 7 A and B. Mobility modifiers, present on certain of the ASOs, are shown in brackets with subscript numbers representing the number of repeat nucleotides present in the mobility modifier. The phosphorylated LSO probes comprised the fluorescent reporter groups dR6G, dROX, dTAMRA, and dR110, as indicated in Table 7 B (see U.S. Pat. No. 6,025,505).

TABLE 7A

Y-Chromosome SNP Probe Sets (ASO probes)

| SNP | designation# | SNP Alleles | ASO1 | ASO2 |
|---|---|---|---|---|
| Y1 | rs3894 | C, T | $[T]_{17}$GTCACCTCTGGGACTGAT (SEQ ID NO: 35) | $[T]_{19}$GTCACCTCTGGGACTGAC (SEQ ID NO: 36) |
| Y6 | rs2032673 | C, T | TGTTTACACTCCTGAAAC (SEQ ID NO: 37) | CTGTTTACACTCCTGAAAT (SEQ ID NO: 38) |
| Y10 | M122 | C, T | $[T]_4$ATTTTCCCCTGAGAGCA (SEQ ID NO: 39) | $[T]_6$ATTTTCCCCTGAGAGCG (SEQ ID NO: 40) |
| Y16 | rs2032598 | C, T | $[T]_5$CAGCAATTTAGTATTGCCC (SEQ ID NO: 41) | $[T]_7$CAGCAATTTAGTATTGCCT (SEQ ID NO: 42) |
| Y20 | rs2020857 | C, T | $[T]_{24}$CAATTAATATTTTTGAAAGAGC (SEQ ID NO: 43) | $[T]_{26}$CAATTAATATTTTTGAAAGAGT (SEQ ID NO: 44) |
| Y40s1a | rs2072422 | A, T | $[T]_{20}$GCGGTGAAGAGTTTGCA (SEQ ID NO: 45) | $[T]_{22}$gCGGTGAAGAGTTTGCT (SEQ ID NO: 46) |
| Y46s1a | rs2196155 | A, G | $[T]_{17}$AGGTTTGAAGTTTTTCTCTA (SEQ ID NO: 47) | $[T]_{19}$AGGTTTGAAGTTTTTCTCTG (SEQ ID NO: 48) |
| Y68s1 | rs3912283 | A, C | TTAATGGAGCTGAGTTCCA (SEQ ID NO: 49) | $[T]_4$AATGGAGCTGAGTTCCC (SEQ ID NO: 50) |
| Y84s1a | rs2032652 | C, T | $[T]_9$CTAAGGTTATGTACAAAAATC TC (SEQ ID NO: 51) | $[T]_{11}$CTAAGGTTATGTACAAAAAT CTT (SEQ ID NO: 52) |

: rs numbers: dsSNP database (see above); M122: see Underhill et al., Ann. Hum. Genet. 65: 43-62, 2001.

TABLE 7 B

Y-Chromosome SNP Probe Sets (labeled LSO probes)

| SNP | LSO probes |
|---|---|
| Y1 | pAATTAGGAAGAGCTGGTACC-dR6G (SEQ ID NO: 53) |
| Y6 | pAAAATATATTTCAGCAAGACA-dR6G (SEQ ID NO: 54) |
| Y10 | pTGAATTAGTATCTCAATTGC-dROX (SEQ ID NO: 55) |

TABLE 7 B-continued

Y-Chromosome SNP Probe Sets (labeled LSO probes)

| SNP | LSO probes |
|---|---|
| Y16 | pGACTTTTACTAATGCATGTG-dTAMRA (SEQ ID NO: 56) |
| Y20 | pTCTTTTAGGTTAATTTAAGTACA-dR110 (SEQ ID NO: 57) |
| Y40s1a | pGTAGATATTTGACCTATAAACT-dTAMRA (SEQ ID NO: 58) |
| Y46s1a | pTTAGGCTTTTGTGCTGA-dR110 (SEQ ID NO: 59) |
| Y68s1 | pGTCAATATTCCCACTGATT-dR110 (SEQ ID NO: 60) |
| Y84s1a | pATCTCTCACTTTGCCTG-dTAMRA (SEQ ID NO: 61) |

The nine SNPs listed in Table 7 were interrogated using the corresponding ligation probe sets in a multiplex PCR-OLA. First, a multiplex PCR amplification was performed using the nine forward and reverse primer sets shown in Table 8A. Ten microliter amplification compositions, comprising 1 μL gDNA (1 ng/μL), 0.5 μL 25 mM MgCl$_2$, 4 μL AmpFlSTR® PCR Reaction Mix (Applied Biosystems Part Number 361680), 1 μL 10× PCR primer mix (shown in Table 8B), 0.2 μL AmpliTaq Gold (5 U/μL), and 3.3 μL water were prepared. The amplification compositions were heated to 95° C. for eleven minutes, thermocycled for thirty-four cycles (95° C. for 30 seconds, 59° C. for 30 seconds, and 72° C. for one minute), heated to 72° C. for ten minutes, then cooled to 4° C.

TABLE 8A

Multiplex PCR Primer Sets

| SNP | forward primer | reverse primer |
|---|---|---|
| Y1 | AAATTGTGAATCTGAAATTTAAGGG (SEQ ID NO: 62) | TTTCAAATAGGTTGACCTGACAA (SEQ ID NO: 63) |
| Y6 | CTGTTCAAATCCAAAAGCT (SEQ ID NO: 64) | AAAAATTTATCTCCCCTTAGCTCT (SEQ ID NO: 65) |
| Y10 | TTTTGGAAATGAATAAATCAAGGT (SEQ ID NO: 66) | CTGTGTTAGAAAAGATAGCTTTATTCAG (SEQ ID NO: 67) |
| Y16 | AGAAAATTTTTGGTAACCCTTAT (SEQ ID NO: 68) | AAAAATTCTTGGTAAGATTTCTCTACAT (SEQ ID NO: 69) |
| Y20 | AACTTACACTCTTTAAGCCATTCC (SEQ ID NO: 70) | TAAACATTACATGAGAAATTGCTGTAC (SEQ ID NO: 71) |
| Y40 | CACGCATCAGTTTATAGGTCAAAT (SEQ ID NO: 72) | GGTGTCCTAAGTGTAAGTAGCAAGTAA (SEQ ID NO: 73) |
| Y46 | TTCTTTATCTGATTATATGTTTGCATTG (SEQ ID NO: 74) | TTAGAACTCACAAAACTGTAATCCC (SEQ ID NO: 75) |
| Y68 | CGGCAACAGATTAGAAACTATG (SEQ ID NO: 76) | TTTATTCAGTGTCTGAGGTTACTGTAGT (SEQ ID NO: 77) |
| Y84 | TCAGCTTCCTGGATTCAGC (SEQ ID NO: 78) | GATCACCAGCAAAGGTAGCT (SEQ ID NO: 79) |

TABLE 8B

10× PCR primer mix formulations.

| Y-SNP | PCR primer (pmole/10 μL) | final OLA probe concentration |
|---|---|---|
| Y1 | 10 | 22.2 |
| Y6 | 10 | 77.8 |
| Y10 | 16 | 888.9 |
| Y16 | 16 | 666.7 |
| Y20 | 10 | 4.4 |
| Y37s1 | 5 | 17.8 |
| Y40s1a | 5 | 53.3 |
| Y46s1a | 5 | 4.0 |
| Y68 | 5 | 4.4 |
| Y84s1a | 5 | 255.6 |

The PCR amplified targets were used in a multiplex OLA reaction as follows. Two ligation reaction compositions (one with Afu ligase, the other with Taq ligase) were formed comprising 4 μL probe mix, 1 μL Afu or Taq ligase (each at 1 U/μL), 2 μL of the amplification reaction composition described above, 1 μL ligation buffer (appropriate for each ligase), and 2 μL water. The two multiplex ligase reaction compositions were cycles 8 times (90° C. for 5 seconds, 46.5° C. for four minutes), heated to 99° C. for ten minutes, then cooled to 4° C. to generate ligation products.

These ligation products were separated by capillary electrophoresis and analyzed as follows. Two µL of the ligation products were combined with 7.5 µL Hi-Di™ formamide and 0.5 µL GS120LIZ size standard (both from Applied Biosystems). These combinations were loaded onto 36 cm capillaries comprising POP-4 polymer on an ABI PRISM® 3100 Genetic Analyzer and separated using the SNP36_POP4 default run module. As shown in FIG. 1, some Y46 misligation products were generated with two samples when Afu ligase (2%) or Taq ligase (10%) was used, while Y10 misligation products were generated only with Taq ligase (25%).

EXAMPLE 8

Effect of Metal Cofactors on the Fidelity of Afu Ligase

The dependence of certain ligases on particular metal cofactors reportedly varies, depending on the ligase(s). To evaluate the effectiveness of manganese and of magnesium ions to serve as cofactors for Afu ligase, a ligation assay was performed in the presence of varying concentrations of the manganese or the magnesium ions, as follows.

A DNA premix was prepared and hybridization complexes formed as described in Example 4, except that the premix comprised 400 nM 5'-phosphate-GCCAAGCTTGCATGC-CTG C-3'Fam (SEQ ID NO:80), 800 nM (−21)M13-primer 5'-TGTAAAACGACGGCCAGT-3' (SEQ ID NO:81) and 800 nM of the artificial M13-derived target 5'-ACATTTTGCTGC CGGTCACGGTTCGAACGTACG-GACG-3' (SEQ ID NO:82) in 20 mM NaCl.

For each of the two metal ions, a series of ten dilutions of either $MnCl_2$ or $MgCl_2$ was prepared (0 to 60 mM). For each metal ion series, 25 µL comprising 0.02 U/µl Afu ligase in 100 mM Tris-HCl pH 7.5, 20 mM DTT, 2 mM ATP, 0.2% Triton X-100 (2× Afu ligation buffer without metal cofactor) was placed into ten thermocycler tubes in parallel (twenty tubes total). To each tube was added 20 µl of one of the metal cofactor dilutions, bringing the volume in each tube to 45 µl. Both sets of tubes were placed on a thermocycler block and maintained at 45° C.

Figure 2:
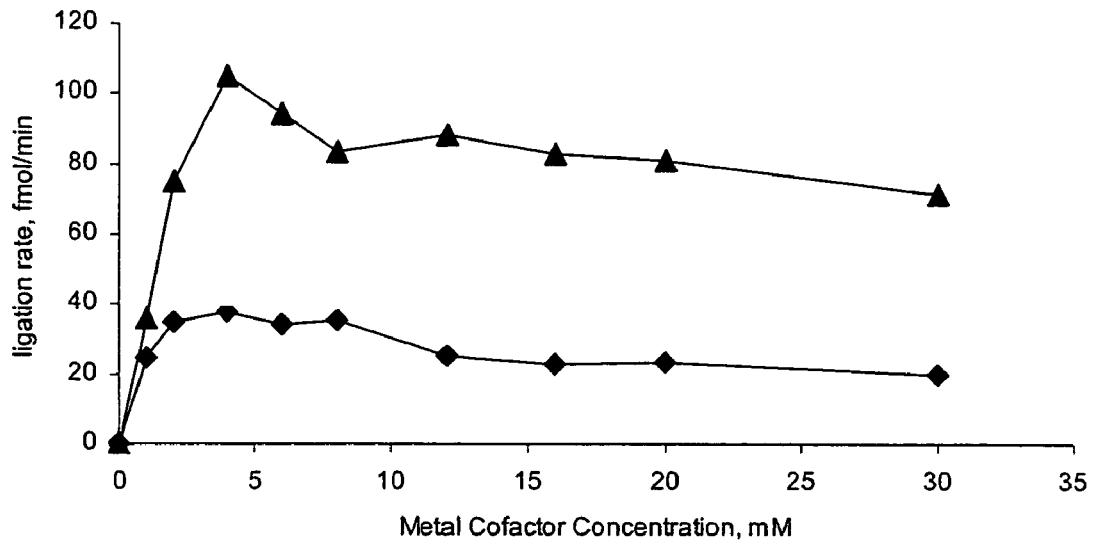
FIG. 2: is a graph showing the effect of varying concentrations of the divalent cation cofactors, magnesium (Mg; shown as diamonds) and manganese (Mn; shown as triangles) on the ligation rate of Afu ligase, as described in Example 8. The x-axis represents the cofactor concentration in mM and the y-axis represents the ligation rate in fmol/min.

The ligation reaction was started by adding 5 µl of the DNA premix to each of the twenty parallel tubes. The resulting 50 µl ligation reaction compositions comprised 1× ligase buffer and 40 nM substrate. A 5 µL aliquot of the reaction composition comprising ligation products was combined with 10 µL of 100 mM EDTA at reaction times of 2 min., 4 min., 8 min., and 20 min. to stop the reaction and the samples were chilled on ice and analyzed as described in Example 4. The results, shown in FIG. 2, suggest that at least under these reaction conditions, Afu ligase can utilize either $Mn^{2+}$ or $Mg^{2+}$ as the metal ion cofactor.

EXAMPLE 9

Thermal Stability Analysis of Afu Ligase

Figure 3:
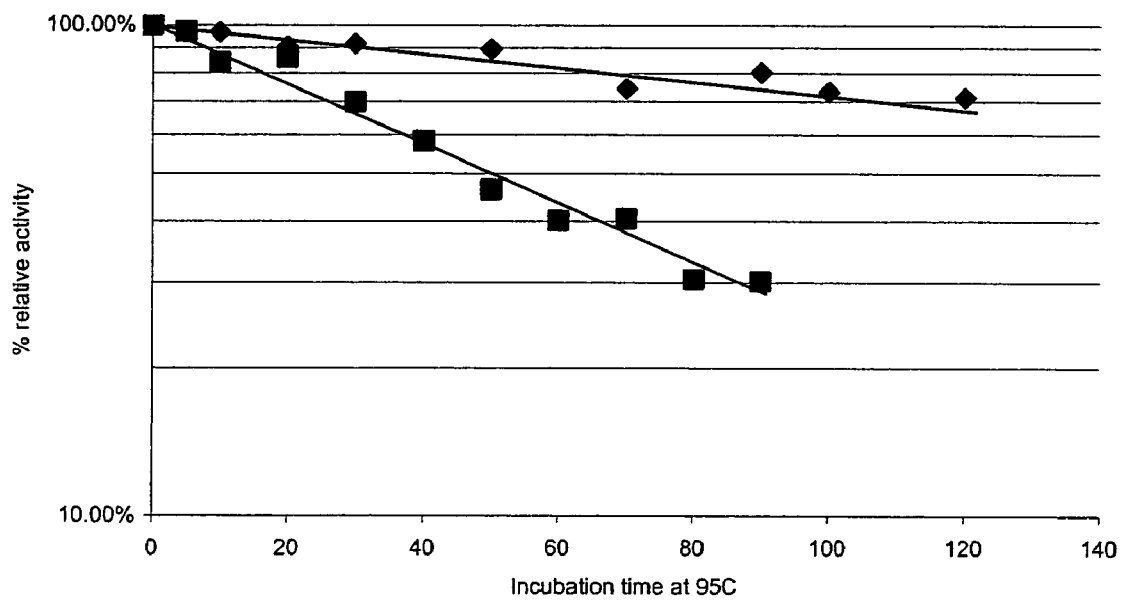
FIG. 3: is a semi-log graph depicting thermal decay curves for Afu ligase (shown as diamonds) and Taq ligase (shown as squares), as described in Example 9. The x-axis represents the incubation time at 95° C. in minutes. The y-axis represents the percent ligase activity remaining in log scale.

To evaluate the thermostability of Afu ligase, a side-by-side comparison with Taq ligase was performed at 95° C. and a thermal decay curve generated. A DNA premix was prepared as described in Example 8. Into two parallel sets of twelve iced tubes was placed either 25 µl of 0.02 U/µl Afu- or Taq ligase in the appropriate ligation buffer (one set of twelve tubes for each ligase). One tube from each set was retained on ice ($t_0$ sample) and the remaining eleven tubes were placed in a thermocycler at temperature of 95° C. One tube from each set was periodically removed from the thermocycler over a two-hour time course and placed on ice. At the end of the two-hour time course, 20 µl of buffer containing 2.5 µl of the appropriate 10× ligation buffer were added to each tube bringing the volume to 45 µl. The tubes were placed on a thermocycler block and maintained at 45° C. Five µL of DNA premix was added to each tube to start generating ligation products. A 5 µL aliquot of the reaction composition comprising ligation products was combined with 10 µL of 100 mM EDTA at reaction times of 2 min., 8 min., 20 min., and 60 min. to stop the reaction and the samples were chilled on ice separated and analyzed as described in Example 4. The thermal decay curve is shown in FIG. 3.

EXAMPLE 10

Screening Mixed Population Tumors for p53 Mutations

Mutations in the human tumor suppressor gene p53 reportedly occur in many human carcinomas and may serve as diagnostic indicators for the presence, progression and/or prognosis of the disease. Point mutations in one of the two p53 genes accompanied by loss of the second p53 allele has been reported in 30-70% of cancers (see, e.g., Ahrendt et al., Proc. Natl. Acad. Sci. 96:7382-87, 1999). To assess the status of two known mutations associated with breast cancer in exon 7 of the human p53 gene according to the present teachings, biopsy tissue is surgically obtained from a patient. Genomic DNA is isolated using conventional methodology including phenol chloroform extraction and ethanol precipitation and the isolated gDNA is PCR amplified and electrophoretically separated, as described in Ahrendt et al., Proc. Natl. Acad. Sci. 96:7382-87, 1999 (see also, Norberg et al., Clin. Chem, 47(5):821-28, 2001).

In this exemplary embodiment, two probe sets are synthesized to interrogate two known p53 exon 7 mutations observed in medullary breast carcinoma, occurring at codon 236 (Y236C, TAC=>TGC) and codon 248 (R248Q, CGG=>CAG; see, e.g., P. deCremoux et al., J. Natl. Canc. Inst. 91:641-43, 1999). The "wild-type" p53 exon 7 sequence is: GTTGGCTCTGACTGTACCAC CATCCACTACAAC TA[1]CATGTGTAACAGTTCCTGCATGGGCGGCATGAA CCG[2]GAGG CCCATCCTCACCATCATCACACTGGAA-GACTCCAG (SEQ ID NO:83) (NCBI Nucleotide Accession No. AF240685), where superscript 1 corresponds to the nucleotide where the 236 point mutation occurs ((mis)ligation junction 1 in this example) and superscript 2 corresponds to the nucleotide where the 248 point mutation occurs ((mis)ligation junction 2 in this example).

The two probes sets used in this illustrative embodiment are shown in Table 9. The two upstream probes in each probe set comprise hybridization tags (shown in brackets) and at their 3' end each comprises a nucleotide that is complementary to one of the two possible target nucleotides at the corresponding mutation site (shown underlined). Each of the downstream probes comprises the fluorescent reporter group Texas Red (shown as—TR). For each probe set there are two possible misligation products, i.e., 3'T:G (probe 84 mismatched with the 236 mutant target nucleic acid sequence or probe 89 mismatched with the 248 wild-type sequence) and 3'C:A (probe 86 mismatched with the wild-type 236 sequence or probe 87 mismatched with the mutant 248 sequence).

TABLE 9

Exemplary p53-236 and p53-248 Probe Sets

| Probe Set | upstream probe | downstream probe |
|---|---|---|
| 236 | [GCTGAGGTCGATGCTGAGGTCGCA]<br>TGCAGGAACTGTTACACATG<u>T</u><br>(SEQ ID NO: 84) probe 84 | AGTTGTAGTGGATGGTGGTA-TR<br>(SEQ ID NO: 85) probe 85 |
| 236 | [GCTGCGATCGATGGTCAGGTGCTG]<br>TGCAGGAACTGTTACACATG<u>C</u><br>(SEQ ID NO: 86) probe 86 | |
| 248 | [GCTGTACCCGATCGCAAGGTGGTC]<br>GATGGTGAGGATGGGCCTC<u>C</u><br>(SEQ ID NO: 87) probe 87 | GGTTCATGCCGCCCATGCAG-TR<br>(SEQ ID NO: 88) probe 88 |
| 248 | [CGCACGATAGGTGGTCTACCGCTG]<br>GATGGTGAGGATGGGCCTC<u>T</u><br>(SEQ ID NO: 89) probe 89 | |

According to the present teachings, *Thermus* species ligases tend to misligated 3'T:G mismatches, while Afu ligase tends to misligated 3'C:A mismatches. Thus, to minimize misligation product formation, two multiplex ligation reaction compositions are formed, comprising either: (a) amplified p53 gDNA; probes 84, 85, 88 and 89; and Afu ligase; or (b) amplified p53 gDNA; probes 85, 86, 87 and 88; and AK16D ligase. The ligation reaction is performed as described in Example 4. The ligation products are then combined with a glass microscope slide gel based "zip-code" array comprising the hybridization tag complements of probes 81, 83, 84, and 86 (Zip1, Zip3, Zip5, and Zip7, respectively), hybridized and detected, essentially as described in Gerry et al., J. Mol. Biol. 292:251-62, 1999. The relative fluorescent intensity detected at the microarray address corresponding to each hybridization tag is compared with a standard curve and the identity and relative quantity of the 236 and 248 markers is determined.

A standard curve can be generated using synthetic target nucleic acid sequences for wild-type p53 exon 7 shown in SEQ ID NO:83 and the corresponding mutant sequences, that is, the nucleic acid sequence of SEQ ID NO:83, but with the middle nucleotide of codon 236 being G ("236-83") or the middle nucleotide of codon 248 being A ("248-83"). For example without limitation, two sets of six ligation reaction compositions are prepared, with the two sets comprising (a) probes 84 and 85; Afu ligase; and either (i) all SEQ ID NO:83, (ii) 80% SEQ ID NO:83 and 20% 236-83, (iii) 60% SEQ ID NO:80 and 40% 236-83, (iv) 40% SEQ ID NO:80 and 60% 236-83, (v) 20% SEQ ID NO:83 and 80% 236-83, or (vi) all 236-83; or (b) probes 85 and 86; AK16D ligase; and either (i) all SEQ ID NO:83, (ii) 80% SEQ ID NO:83 and 20% 236-83, (iii) 60% SEQ ID NO:83 and 40% 236-83, (iv) 40% SEQ ID NO:83 and 60% 236-83, (v) 20% SEQ ID NO:83 and 80% 236-83, or (vi) all 236-83. The ligation reaction, microarray detection (but using a separate microarray for each set of ligation products), identification and quantification are performed as described in this example, and the detected fluorescent intensity plotted to generate a standard curve. Those in the art understand that similar standard curves can be generated for any target nucleic acid sequence and corresponding probe set. Using such standard curves, the quantity of the corresponding target nucleotide present in the sample can be inferred or extrapolated.

Those in the art will also appreciate that the current teachings can be applied not only to-identifying and quantifying known p53 mutations in human tumors and cancer screening/detection assays in a wide variety of tissues and/or organs (see, e.g., Overholtzer et al., Proc. Natl. Acad. Sci. 100:11547-52, 2003; Ahrendt et al., Proc. Natl. Acad. Sci. 96:7382-87, 1999), but also a wide variety of mutations in tumor suppressor genes (including without limitation, RB, the P16 gene, and the like), cellular oncogenes or proto-oncogenes (including without limitation, sis, ras, abl, src, fos, jun, and the like); and also virtually any other heritable or somatic mutation, including without limitation, chromosomal translocations, insertion mutations, deletion mutations, and the like.

EXAMPLE 11

Human Identification from a Crime Scene Forensics Sample

This illustrative embodiment demonstrates one exemplary method for identifying the donor of genetic material obtained from a crime scene. In this example, a fresh blood sample is obtained from the scene of a crime with a single female victim and an unknown number of male assailants.

The gDNA is obtained from the sample using BloodPrep™ Chemistry on the ABI PRISM® 6700 Nucleic Acid Workstation, following the manufacturer's protocols (both from Applied Biosystems). The Y-chromosome SNPs Y1, Y6, Y10, Y16, Y20, and Y68 are amplified in a six-plex PCR using the appropriate primer sets, as described in Example 7. One aliquot of the PCR amplified targets is combined with Afu ligase and the probe sets corresponding to the Y1, Y10 and Y16 SNPs (shown in Tables 7A and 7B) to form a first ligation reaction composition. A second aliquot of PCR amplified targets is combined with Taq ligase and the probe sets corresponding to the Y16, Y20, and Y68 SNPs (shown in Tables 7A and 7B), to decrease the generation of misligation products. The two ligation reaction compositions are subjected to multiple cycles of ligation in parallel, and the resulting amplified ligation products are separated and analyzed using on the ABI PRISM® 3100 Genetic Analyzer, as described in Example 7. The suspect identifications are verified using the AmpFlSTR® Profiler Plus PCR and the AmpFlSTR Cofiler® PCR Amplification Kits to generate amplified CODIS STR loci and the ABI PRISM® 3100 Avant Genetic Analyzer and GeneMapper® ID software (all from Applied Biosystems), according to the manufacturer's instructions.

Although the disclosed teachings has been described with reference to various applications, methods, and compositions, it will be appreciated that various changes and modifications may be made without departing from the teachings herein. The foregoing examples are provided to better illustrate the disclosed teachings and are not intended to limit the scope of the teachings herein.

We claim:

1. A method for identifying at least one first target nucleotide and at least one second target nucleotide in a mixed population, comprising:

forming a first ligation reaction composition comprising (a) at least one first target nucleic acid sequence, (b) at least one first ligation probe set comprising at least one first probe and at least one second probe, wherein the at least one first probe comprises at least one first target-specific portion and the at least one second probe comprises at least one second target-specific portion, and (c) at least one first ligase;

forming a second ligation reaction composition comprising (a) at least one second target nucleic acid sequence, (b) at least one second ligation probe set comprising at least one first probe and at least one second probe, wherein the at least one first probe comprises at least one target-specific portion and the at least one second probe comprises at least one target-specific portion, and (c) at least one second ligase;

subjecting the first ligation reaction composition to at least one cycle of ligation to generate at least one first ligation product;

subjecting the second ligation reaction composition to at least one cycle of ligation to generate at least one second ligation product; and identifying the at least one first target nucleotide, the at least one second target nucleotide, or the at least one first target nucleotide and the at least one second target nucleotide in the mixed population.

2. The method of claim 1, wherein the subjecting the first ligation reaction composition to at least one cycle of ligation and the subjecting the second ligation reaction composition to at least one cycle of ligation are performed in parallel.

3. The method of claim 1, wherein the subjecting the first ligation reaction composition to at least one cycle of ligation and the subjecting the second ligation reaction composition to at least one cycle of ligation are performed separately.

4. The method of claim 1, wherein the forming the first ligation reaction composition and the forming the second ligation reaction composition are performed in parallel.

5. The method of claim 1, wherein the forming the first ligation reaction composition and the forming the second ligation reaction composition are performed separately.

6. The method of claim 1, wherein the at least one first ligation product, the at least one second ligation product, or the at least one first ligation product and the at least one second ligation product, further comprises at least one primer-binding portion, at least one reporter group, at least one mobility modifier, at least one hybridization tag, at least one reporter probe-binding portion, at least one affinity tag, or combinations thereof.

7. The method of claim 6, wherein the identifying comprises (a) detecting the at least one reporter group of the at least one first ligation product, the at least one reporter group of the at least one second ligation product, or the at least one reporter group of the at least one first ligation product, the at least one reporter group of the at least one second ligation product and (b) quantifying the at least one reporter group of the at least one first ligation product, the at least one reporter group of the at least one second ligation product, or the at least one reporter group of the at least one first ligation product and the at least one reporter group of the at least one second ligation product.

8. The method of claim 6, further comprising combining at least one first ligation product, at least one second ligation product, or at least one first ligation product and at least one second ligation product with at least one reporter probe.

9. The method of claim 8, wherein the identifying comprises detecting the at least one reporter probe of the first ligation product, at least part of the at least one reporter probe corresponding to the first ligation product, the at least one reporter probe of the at least one second ligation product, at least part of the at least one reporter probe corresponding to the second ligation product, or combinations thereof, and quantifying the at least one first ligation product, the at least one second ligation product, or the at least one first ligation product and the at least one second ligation product.

10. The method of claim 6, further comprising, combining at least one hybridization tag complement comprising at least one reporter group with: the at least one first ligation product, the at least one second ligation product, or the at least one first ligation product and the at least one second ligation product; and wherein the identifying comprises detecting the at least one reporter group of the at least one hybridization tag complement, at least part of the hybridization tag complement, or combinations thereof.

11. The method of claim 1, wherein the at least one first ligase comprises Afu ligase, including enzymatically active mutants or variants thereof.

12. The method of claim 11, wherein the at least one second ligase comprises at least one thermostable ligase, including enzymatically active mutants or variants thereof, but not Afu ligase, including enzymatically active mutants or variants thereof.

13. The method of claim 12, wherein the at least one thermostable ligase comprises at least one of: Taq ligase, *Thermus* species ligase AK16D, Tth ligase, Tsc ligase, Tfi ligase, or combinations thereof.

14. The method of claim 1, wherein the at least one cycle of ligation comprises a multiplicity of cycles of ligation.

15. The method of claim 1, wherein the identifying comprises separating the at least one first ligation product, the at least one second ligation product, or the at least one first ligation product and the at least one second ligation product, using at least one mobility dependent analytical technique.

16. The method of claim 15, wherein the at least one mobility dependent analytical technique comprises capillary electrophoresis.

17. The method of claim 6, wherein the identifying comprises binding or annealing at least one first ligation product, at least one second ligation product, or at least one first ligation product and at least one second ligation product, to at least one substrate.

18. The method of claim 17, wherein the at least one substrate comprises at least one microarray.

19. The method of claim 6, further comprising amplifying the at least one first ligation product, the at least one second ligation product, or the at least one first ligation product and the at least one second ligation product, to generate at least one amplified first ligation product, at least one amplified second ligation product, or at least one amplified first ligation product and at least one amplified second ligation product.

20. The method of claim 19, wherein the at least one amplified first ligation product, the at least one amplified second ligation product, or the at least one amplified first ligation product and the at least one amplified second ligation product, further comprises at least one primer-binding portion, at least one reporter group, at least one mobility modifier, at least one hybridization tag, at least one reporter probe-binding portion, at least one affinity tag, or combinations thereof.

21. The method of claim 20, wherein the identifying comprises detecting the at least one reporter group of the at least one amplified first ligation product and the at least one reporter group of the at least one amplified second ligation product, and quantifying the at least one amplified first ligation product and the at least one amplified second ligation product.

22. The method of claim 20, further comprising, combining at least one hybridization tag complement comprising at least one reporter group with at least one amplified ligation product; and wherein the identifying comprises detecting the at least one reporter group of the at least one hybridization tag complement.

23. The method of claim 20, further comprising combining the at least one amplified first ligation product, the at least one amplified second ligation product, or the at least one amplified first ligation product and the at least one amplified second ligation product, with at least one reporter probe.

24. The method of claim 23, wherein the identifying comprises detecting at least one reporter probe, at least part of at least one reporter probe, or at least one reporter probe and at least part of at least one reporter probe, and comparing the ratio of the amplified ligation products of at least one ligation probe set.

25. The method of claim 20, wherein the identifying comprises separating the at least one amplified first ligation product, the at least one amplified second ligation product, or the at least one amplified first ligation product and the at least one amplified second ligation product, using at least one mobility dependent analytical technique.

26. The method of claim 25, wherein the at least one mobility dependent analytical technique comprises capillary electrophoresis.

27. The method of claim 20, wherein the identifying comprises binding or annealing at least one amplified first ligation product, at least one amplified second ligation product, or at least one amplified first ligation product and at least one amplified second ligation product, to at least one substrate.

28. The method of claim 27, wherein the at least one substrate comprises at least one microarray.

29. The method of claim 6, wherein the identifying the at least one first target nucleotide, the at least one second target nucleotide, or the at least one first target nucleotide and the at least one second target nucleotide comprises quantifying the at least one first ligation product, the at least one second ligation product, or the at least one first ligation product and the at least one second ligation product.

30. The method of claim 29, wherein the quantifying comprises quantitative polymerase chain reaction (Q-PCR).

31. The method of claim 30, wherein the Q-PCR comprises at least one 5'-exonuclease probe, at least one molecular beacon probe, at least one peptide nucleic acid (PNA) probe, at least one Locked Nucleic Acid probe, at least one nucleic acid dye, or combinations thereof.

32. A method for identifying at least one first target nucleotide and at least one second target nucleotide in a mixed population, comprising:
    amplifying the mixed population to generate at least one amplified first target nucleotide and at least one amplified second target nucleotide;
    forming a first ligation reaction composition comprising (a) the at least one amplified first target nucleotide, (b) at least one first ligation probe set comprising at least one first probe and at least one second probe, wherein the at least one first probe comprises at least one first target-specific portion and the at least one second probe comprises at least one second target-specific portion, and (c) Afu ligase, including enzymatically active mutants or variants thereof;
    forming a second ligation reaction composition comprising (a) the at least one amplified second target nucleotide, (b) at least one second ligation probe set comprising at least one first probe and at least one second probe, wherein the at least one first probe comprises at least one first target-specific portion and the at least one second probe comprises at least one second target-specific portion, and (c) at least one second thermostable ligase, including enzymatically active mutants or variants thereof, but not Afu ligase, including enzymatically active mutants or variants thereof;
    subjecting the first ligation reaction composition to a multiplicity of cycles of ligation to generate at least one first ligation product;
    subjecting the second ligation reaction composition to a multiplicity of cycles of ligation to generate at least one second ligation product; and
    identifying the at least one first target nucleotide, the at least one second target nucleotide, or the at least one first target nucleotide and the at least one second target nucleotide in the mixed population, wherein the identifying comprises separating the at least one first ligation product, at least part of the first ligation product, the at least one second ligation product, at least part of the second ligation product, or combinations thereof, using capillary electrophoresis.

33. The method of claim 32, wherein the at least one first ligation product, the at least one second ligation product, or the at least one first ligation product and the at least one second ligation product, comprises at least one reporter group, at least one mobility modifier, at least one hybridization tag, at least one reporter probe-binding portion, at least one affinity tag, or combinations thereof.

34. The method of claim 32, wherein the subjecting the first ligation reaction composition to a multiplicity of cycles of ligation and the subjecting the second ligation reaction composition to a multiplicity of cycles of ligation are performed in parallel.

35. The method of claim 32, wherein the subjecting the first ligation reaction composition to a multiplicity of cycles of ligation and the subjecting the second ligation reaction composition to a multiplicity of cycles of ligation are performed separately.

36. The method of claim 32, wherein the forming the first ligation reaction composition and the forming the second ligation reaction composition are performed in parallel.

37. The method of claim 32, wherein the forming the first ligation reaction composition and the forming the second ligation reaction composition are performed separately.

38. A method for identifying at least one first target nucleotide and at least one second target nucleotide in a mixed population, comprising:
    at least one step for identifying a nucleic macid position at least one first target nucleotide, at least one second target nucleotide, or at least one first target nucleotide and at least one second target nucleotide;
    at least one step for generating at least one first ligation product, at least one second ligation product, or at least one first ligation product and at least one second ligation product; and
    at least one step for identifying the at least one first target nucleotide, the at least one second target nucleotide, or the at least one first target nucleotide and the at least one second target nucleotide.

39. The method of claim 38, wherein (a) the at least one step for identifying a nucleic acid position the at least one first nucleotide and the at least one step for identifying a nucleic acid position the at least one second target nucleotide are separate, (b) the at least one step for generating at least one first ligation product and the at least one step for generating at least one second ligation product are separate, or (c) the at least one step for identifying a nucleic acid position the at least one first nucleotide and the at least one step for identifying a nucleic acid position the at least one second target nucleotide are separate and the at least one step for generating at least one first ligation product and the at least one step for generating at least one second ligation product are separate.

40. The method of claim 38, further comprising at least one step for amplifying the at least one first ligation product, the at least one second ligation product, or the at least one first ligation product and the at least one second ligation product, and wherein the identifying comprises detecting the at least one amplified first ligation product, the at least one amplified second ligation product, or the at least one amplified first ligation product and the at least one amplified second ligation product.

41. The method of claim 40, further comprising at least one step for digesting the at least one amplified ligation product.

42. The method of claim 40, further comprising at least one step for digesting the at least one ligation product.

43. A method for identifying at least one first target nucleotide and at least one second target nucleotide in a mixed population, comprising:
- at least one step for amplifying at least one first target nucleotide, at least one second target nucleotide, or at least one first target nucleotide and at least one second target nucleotide;
- at least one step for identifying a nucleic acid position the at least one first target nucleotide, the at least one amplified first target nucleotide, the at least one second target nucleotide, the at least one amplified second target nucleotide, or combinations thereof;
- at least one step for generating at least one first ligation product, at least one second ligation product, or at least one first ligation product and at least one second ligation product; and
- at least one step for identifying the at least one first target nucleotide, the at least one second target nucleotide, or the at least one first target nucleotide and the at least one second target nucleotide in the mixed population.

* * * * *

SEQUENCE LISTING

<160> NUMBER OF SEQ ID NOS: 91

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: Synthetic
      template

<400> SEQUENCE: 1
acattttgct gccggtcacg gttcgaacgt acggacg                              37

<210> SEQ ID NO 2
<211> LENGTH: 37
<212> TYPE: DNA
<213> ORGANISM: Artificial Sequence
<220> FEATURE:
<223> OTHER INFORMATION: Description of Artificial Sequence: Synthetic
      template

<400> SEQUENCE: 2
acattttgct gccggtctcg gttcgaacgt acggacg                              37

<210> SEQ ID NO 3
<211> LENGTH: 37
<212> TYPE: DNA
<213> ORGANISM: Artificial Sequence
<220> FEATURE:
<223> OTHER INFORMATION: Description of Artificial Sequence: Synthetic
      template

<400> SEQUENCE: 3
acattttgct gccggtcgcg gttcgaacgt acggacg                              37

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: Synthetic
      template

<400> SEQUENCE: 4
acattttgct gccggtcccg gttcgaacgt acggacg                              37

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
tgtaaaacga cggccagt                                                  18

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base

```
<222> LOCATION: (1)
<223> OTHER INFORMATION: Phosphorylated G

<400> SEQUENCE: 6
gccaagcttc gatgcctgc                                                   19

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tttttgtaaa acgacggcca ga                                               22

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8 ttttttttg taaaacgacg gccagc                                            26

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
tttttttttt tttgtaaaac gacggccagg                                       30

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
acaacaaagg tactttagca cgcgtcacag cg                                    32

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
acaacaaagg tactttagga cgcgtcacag cg                                    32

<210> SEQ ID NO 12
<211> LENGTH: 40
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 12
ccgccacttc tcaaacgaca tctataaact ggatatttga         40

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ccgccacttc tcaaacgtca tctataaact ggatatttga         40

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
aatccaaact tcaaaaagag acaatccgaa aacacgact         39

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
aatccaaact tcaaaaagag ataatccgaa aacacgact         39

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tcgacggttc attttatgag tccgaaatgt tgtcacg         37

<210> SEQ ID NO 17
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tcgacggttc attttatgcg tccgaaatgt tgtcacg         37

<210> SEQ ID NO 18
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 18
gattccaata catgttttta gaatagagag tgaaacggac                               40

<210> SEQ ID NO 19
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gattccaata catgttttta gagtagagag tgaaacggac                               40

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
tgttgtttcc atgaaatcc                                                      19

<210> SEQ ID NO 21
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
tttttttttt ttgtttcatg aaatcg                                              26

<210> SEQ ID NO 22
<211> LENGTH: 13
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: Phosphorylated T

<400> SEQUENCE: 22
tgcgcagtgt cgc                                                            13

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
tttttttttt tttttttttt ttgcggtgaa gagtttgca                                39

<210> SEQ ID NO 24
<211> LENGTH: 27
<212> TYPE: DNA
<213> ORGANISM: Artificial Sequence
```

-continued

```
<220> FEATURE:
<223> OTHER INFORMATION: Description of Artificial Sequence: Synthetic
      probe

<400> SEQUENCE: 24
tttttttttt gcggtgaaga gtttgct                                              27

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: Phosphorylated G

<400> SEQUENCE: 25
gtagatattt gacctataaa ct                                                   22

<210> SEQ ID NO 26
<211> LENGTH: 27
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 26
tttttttagg tttgaagttt ttctcta                                              27

<210> SEQ ID NO 27
<211> LENGTH: 39
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 27
tttttttttt tttttttta ggtttgaagt ttttctctg                                  39

<210> SEQ ID NO 28
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: Phosphorylated T

<400> SEQUENCE: 28
ttaggctttt gtgctga                                                         17

<210> SEQ ID NO 29
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
```
agctgccaag taaaatact                                                19

<210> SEQ ID NO 30
<211> LENGTH: 25
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
tttttttttt ttcaagtaaa atacg                                         25

<210> SEQ ID NO 31
<211> LENGTH: 18
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: Phosphorylated C

<400> SEQUENCE: 31
caggctttac aacagtgc                                                 18

<210> SEQ ID NO 32
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 32
ctaaggttat gtacaaaaat ctc                                           23

<210> SEQ ID NO 33
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 33
tttttttttt tctaaggtta tgtacaaaaa tctt                               34

<210> SEQ ID NO 34
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: Phosphorylated A

<400> SEQUENCE: 34
atctctcact ttgcctg                                                  17

<210> SEQ ID NO 35
<211> LENGTH: 35
<212> TYPE: DNA

```
<213> ORGANISM: Artificial Sequence
<220> FEATURE:
<223> OTHER INFORMATION: Description of Artificial Sequence: Synthetic
      probe

<400> SEQUENCE: 35
tttttttttt tttttttgtc acctctggga ctgat                                    35

<210> SEQ ID NO 36
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 36
tttttttttt ttttttttg tcacctctgg gactgac                                   37

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
tgtttacact cctgaaac                                                       18

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
ctgtttacac tcctgaaat                                                      19

<210> SEQ ID NO 39
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
ttttattttc ccctgagagc a                                                   21

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40 tttttttattt tccctgaga gcg                                                 23

<210> SEQ ID NO 41
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 41
tttttcagca atttagtatt gccc                                              24

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
tttttttcag caatttagta ttgcct                                            26

<210> SEQ ID NO 43
<211> LENGTH: 46
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
tttttttttt tttttttttt ttttcaatta atattttga aagagc                       46

<210> SEQ ID NO 44
<211> LENGTH: 48
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
tttttttttt tttttttttt tttttcaat taatattttt gaaagagt                     48

<210> SEQ ID NO 45
<211> LENGTH: 37
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
tttttttttt tttttttttt gcggtgaaga gtttgca                                37

<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
tttttttttt tttttttttt ttgcggtgaa gagtttgct                              39

<210> SEQ ID NO 47
<211> LENGTH: 37
<212> TYPE: DNA
<213> ORGANISM: Artificial Sequence
<220> FEATURE:
```

<223> OTHER INFORMATION: Description of Artificial Sequence: Synthetic
      probe

<400> SEQUENCE: 47
tttttttttt tttttttagg tttgaagttt ttctcta                              37

<210> SEQ ID NO 48
<211> LENGTH: 39
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
tttttttttt ttttttttta ggtttgaagt ttttctctg                            39

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
ttaatggagc tgagttcca                                                  19

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 50
ttttaatgga gctgagttcc c                                               21

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 51 ttttttttttc taaggttatg tacaaaaatc tc                                  32

<210> SEQ ID NO 52
<211> LENGTH: 34
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 52
tttttttttt tctaaggtta tgtacaaaaa tctt                                 34

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic

```
            probe
<220> FEATURE:
<221> NAME/KEY: modified_base
<222> LOCATION: (1)
<223> OTHER INFORMATION: Phosphorylated A

<400> SEQUENCE: 53
aattaggaag agctggtacc                                               20

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: Phosphorylated A

<400> SEQUENCE: 54
aaaatatatt tcagcaagac a                                             21

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: Phosphorylated T

<400> SEQUENCE: 55
tgaattagta tctcaattgc                                               20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: Phosphorylated G

<400> SEQUENCE: 56 gactttact aatgcatgtg                                                20

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: Phosphorylated T

<400> SEQUENCE: 57
tcttttaggt taatttaagt aca                                           23
```

<210> SEQ ID NO 58
<211> LENGTH: 22
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: Phosphorylated G

<400> SEQUENCE: 58
gtagatattt gacctataaa ct                                            22

<210> SEQ ID NO 59
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: Phosphorylated T

<400> SEQUENCE: 59
ttaggctttt gtgctga                                                  17

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: Phosphorylated G

<400> SEQUENCE: 60
gtcaatattc ccactgatt                                                19

<210> SEQ ID NO 61
<211> LENGTH: 17
<212> TYPE: DNA
<213> ORGANISM: Artificial Sequence
<220> FEATURE:
<223> OTHER INFORMATION: Description of Artificial Sequence: Synthetic
      probe
<220> FEATURE:
<221> NAME/KEY: modified_base
<222> LOCATION: (1)
<223> OTHER INFORMATION: Phosphorylated A

<400> SEQUENCE: 61
atctctcact ttgcctg                                                  17

<210> SEQ ID NO 62
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
aaattgtgaa tctgaaattt aaggg                                         25

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 63
tttcaaatag gttgacctga caa                                            23

<210> SEQ ID NO 64
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 64
ctgttcaaat ccaaaagct                                                 19

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 65
aaaaatttat ctccccttag ctct                                           24

<210> SEQ ID NO 66
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
ttttggaaat gaataaatca aggt                                           24

<210> SEQ ID NO 67
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
ctgtgttaga aaagatagct ttattcag                                       28

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
agaaaatttt tggtaaccct tat                                            23

<210> SEQ ID NO 69
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
aaaaattctt ggtaagattt ctctacat                                        28

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
aacttacact ctttaagcca ttcc                                            24

<210> SEQ ID NO 71
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
taaacattac atgagaaatt gctgtac                                         27

<210> SEQ ID NO 72
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
cacgcatcag tttataggtc aaat                                            24

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 73
ggtgtcctaa gtgtaagtag caagtaa                                         27

<210> SEQ ID NO 74
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 74
ttctttatct gattatatgt ttgcattg                                        28

```
<210> SEQ ID NO 75
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
ttagaactca caaaactgta atccc                                          25

<210> SEQ ID NO 76
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
cggcaacaga ttagaaacta tg                                             22

<210> SEQ ID NO 77
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
tttattcagt gtctgaggtt actgtagt                                       28

<210> SEQ ID NO 78
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tcagcttcct ggattcagc                                                 19

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gatcaccagc aaaggtagct                                                20

<210> SEQ ID NO 80
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
gccaagcttg catgcctgc                                                 19

<210> SEQ ID NO 81
```

```
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
tgtaaaacga cggccagt                                                      18

<210> SEQ ID NO 82
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 82
acattttgct gccggtcacg gttcgaacgt acggacg                                 37

<210> SEQ ID NO 83
<211> LENGTH: 110
<212> TYPE: DNA
<213> ORGANISM: Homo sapiens

<400> SEQUENCE: 83
gttggctctg actgtaccac catccactac aactacatgt gtaacagttc ctgcatgggc        60
ggcatgaacc ggaggcccat cctcaccatc atcacactgg aagactccag               110

<210> SEQ ID NO 84
<211> LENGTH: 45
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 84
gctgaggtcg atgctgaggt cgcatgcagg aactgttaca catgt                        45

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 85
agttgtagtg gatggtggta                                                    20

<210> SEQ ID NO 86
<211> LENGTH: 45
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 86
gctgcgatcg atggtcaggt gctgtgcagg aactgttaca catgc                        45

<210> SEQ ID NO 87
```

-continued

```
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 87
gctgtacccg atcgcaaggt ggtcgatggt gaggatgggc ctcc            44

<210> SEQ ID NO 88
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 88
ggttcatgcc gcccatgcag                                       20

<210> SEQ ID NO 89
<211> LENGTH: 44
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 89
cgcacgatag gtggtctacc gctggatggt gaggatgggc ctct            44

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
catatgatgt tgtttgccga gtttg                                 25

<210> SEQ ID NO 91
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
tcgactcatt gtctctttac ctcgaactg                             29
```